(12) United States Patent
Thomas

(10) Patent No.: US 8,319,030 B2
(45) Date of Patent: Nov. 27, 2012

(54) SOYBEAN CULTIVAR 3317361

(75) Inventor: James Dolphin Thomas, DeWitt, AR (US)

(73) Assignee: Bayer CropScience LP, Research Triangle Park, NC (US)

( * ) Notice: Subject to any disclaimer, the term of this patent is extended or adjusted under 35 U.S.C. 154(b) by 125 days.

(21) Appl. No.: 12/697,064

(22) Filed: Jan. 29, 2010

(65) Prior Publication Data

US 2011/0191879 A1    Aug. 4, 2011

(51) Int. Cl.
  *A01H 1/00* (2006.01)
  *A01H 4/00* (2006.01)
  *A01H 5/00* (2006.01)
  *A01H 5/10* (2006.01)
  *C12N 15/82* (2006.01)

(52) U.S. Cl. ........ 800/312; 435/415; 800/260; 800/298; 800/300; 800/301; 800/302

(58) Field of Classification Search ........................ None
  See application file for complete search history.

(56) References Cited

U.S. PATENT DOCUMENTS

| | | | |
|---|---|---|---|
| 5,304,719 A | | 4/1994 | Segebart |
| 5,367,109 A | | 11/1994 | Segebart |
| 5,523,520 A | | 6/1996 | Hunsperger et al. |
| 5,850,009 A | | 12/1998 | Kevern |
| 5,968,830 A | | 10/1999 | Dan et al. |
| 6,965,061 B2 * | | 11/2005 | Shannon ........................ 800/312 |

OTHER PUBLICATIONS

Eshed, et al., 1996. Less-than-additive epistatic interactions of quantitative trait loci in tomato. Genetics 143:1807-1817.
Kraft, et al., 2000. Linkage disequilibrium and fingerprinting in sugar beet. Theor. App. Genet. 101:323-326.
Willmot, et al., 1989. Genetic analysis of brown stem rot resistance in soybean. Crop Sci. 29:672-674.
Poehlman, J.M. and Sleper, D.A., Methods in Plant Breeding, in Breeding Field Crops, 4$^{th}$ ed. (1995), Iowa State University Press, pp. 172-174.
Narvel, et al., 2001. A Retrospective DNA Marker Assessment of the Development of Insect Resistant Soybean. Crop Sci. 41:1931-1939.
Goldman, et al., 1994. Molecular Markers Associated with Maize Kernel Oil Concentration in an Illinois High Protein x Illinois Low Protein Cross. Crop Sci. 34: 908-915.
US PVP, Certificate No. 009800152, Granted Application of Hornbeck Seed Co., Inc., Jul. 19, 2002.

\* cited by examiner

*Primary Examiner* — David H Kruse

(57) ABSTRACT

A soybean cultivar designated 3317361 is disclosed. The invention relates to the seeds of soybean cultivar 3317361, to the plants of soybean 3317361, to plant parts of soybean cultivar 3317361, and to methods for producing a soybean plant produced by crossing soybean cultivar 3317361 with itself or with another soybean variety. The invention also relates to methods for producing a soybean plant containing in its genetic material one or more transgenes and to the transgenic soybean plants and plant parts produced by those methods. This invention also relates to soybean cultivars, or breeding cultivars, and plant parts derived from soybean variety 3317361, to methods for producing other soybean cultivars, lines or plant parts derived from soybean cultivar 3317361, and to the soybean plants, varieties, and their parts derived from use of those methods. The invention further relates to hybrid soybean seeds, plants, and plant parts produced by crossing the cultivar 3317361 with another soybean cultivar.

23 Claims, No Drawings

SOYBEAN CULTIVAR 3317361

BACKGROUND OF THE INVENTION

The present invention relates to a new and distinctive soybean cultivar, designated 3317361. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of soybean plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selection, selfing and mutations. Therefore, a breeder will never develop the same line, or even very similar lines, having the same soybean traits from the exact same parents.

Each year, the plant breeder selects the germplasm to advance to the next generation. This germplasm is grown under unique and different geographical, climatic and soil conditions and further selections are then made during and at the end of the growing season. The cultivars that are developed are unpredictable because the breeder's selection occurs in unique environments with no control at the DNA level, and with millions of different possible genetic combinations being generated. A breeder of ordinary skill in the art cannot predict the final resulting lines he develops, except possibly in a very gross and general fashion. The same breeder cannot produce the same cultivar twice by using the same original parents and the same selection techniques. This unpredictability results in the expenditure of large amounts of research monies to develop superior new soybean cultivars.

The development of new soybean cultivars requires the development and selection of soybean varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents that possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Soybean, Glycine max (L), is an important and valuable field crop. Thus, a continuing goal of soybean plant breeders is to develop stable, high yielding soybean cultivars that are agronomically sound. The reasons for this goal are obviously to maximize the amount of grain produced on the land used and to supply food for both animals and humans. To accomplish this goal, the soybean breeder must select and develop soybean plants that have traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided a new soybean cultivar designated 3317361. This invention thus relates to the seeds of soybean cultivar 3317361, to the plants of soybean cultivar 3317361 and to methods for producing a soybean plant produced by crossing the soybean cultivar 3317361 with itself or another soybean cultivar, and the creation of variants by mutagenesis or transformation of soybean cultivar 3317361.

Thus, any such methods using the soybean cultivar 3317361 are part of this invention: selfing, backcrosses, hybrid production, crosses to populations, and the like. All plants produced using soybean cultivar 3317361 as at least one parent are within the scope of this invention. Advantageously, the soybean cultivar could be used in crosses with other, different, soybean plants to produce first generation ($F_1$) soybean hybrid seeds and plants with superior characteristics.

In another aspect, the present invention provides for single or multiple gene converted plants of soybean cultivar 3317361. The transferred gene(s) may preferably be a dominant or recessive allele. Preferably, the transferred gene(s) will confer such traits as herbicide resistance, insect resistance, resistance for bacterial, fungal, or viral disease, male fertility, male sterility, enhanced nutritional quality, modified fatty acid metabolism, modified carbohydrate metabolism, modified seed yield, modified oil percent, modified protein percent, modified lodging resistance, modified shattering, modified iron-deficiency chlorosis, and industrial usage. The gene may be a naturally occurring soybean gene or a transgene introduced through genetic engineering techniques.

In another aspect, the present invention provides regenerable cells for use in tissue culture of soybean plant 3317361. The tissue culture will preferably be capable of regenerating plants having all the physiological and morphological characteristics of the foregoing soybean plant, and of regenerating plants having substantially the same genotype as the foregoing soybean plant. Preferably, the regenerable cells in such tissue cultures will be embryos, protoplasts, meristematic cells, callus, pollen, leaves, ovules, anthers, cotyledons, hypocotyl, pistils, roots, root tips, flowers, seeds, petiole, pods, or stems. Still further, the present invention provides soybean plants regenerated from the tissue cultures of the invention.

In addition to the exemplary aspects and embodiments described above, further aspects and embodiments will become apparent by study of the following descriptions.

DEFINITIONS

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Alter. The utilization of up-regulation, down-regulation, or gene silencing.

Brown Stem Rot. This is a visual disease score from 1 to 9 comparing all genotypes in a given test. The score is based on leaf symptoms of yellowing and necrosis caused by brown stem rot. Visual scores range from a score of 9, which indicates no symptoms, to a score of 1 which indicates severe symptoms of leaf yellowing and necrosis.

Cell. Cell as used herein includes a plant cell, whether isolated, in tissue culture or incorporated in a plant or plant part.

Cotyledon. A cotyledon is a type of seed leaf. The cotyledon contains the food storage tissues of the seed.

Embryo. The embryo is the small plant contained within a mature seed.

Emergence. This score indicates the ability of the seed to emerge when planted 3" deep in sand at a controlled temperature of 25° C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a 1 score indicates a very poor rate and percent of emergence.

$F_3$. The "$F_3$" symbol denotes a generation resulting from the selfing of the $F_2$ generation along with selection for type and rogueing of off-types. The "F" number is a term commonly used in genetics, and designates the number of the filial generation. The "$F_3$" generation denotes the offspring resulting from the selfing or self mating of members of the generation having the next lower "F" number, viz. the $F_2$ generation.

Gene. As used herein, "gene" refers to a segment of nucleic acid. A gene can be introduced into a genome of a species, whether from a different species or from the same species, using transformation or various breeding methods.

Gene Silencing. The interruption or suppression of the expression of a gene at the level of transcription or translation.

Genotype. Refers to the genetic constitution of a cell or organism.

Hilum. This refers to the scar left on the seed that marks the place where the seed was attached to the pod prior to the seed being harvested.

Hypocotyl. A hypocotyl is the portion of an embryo or seedling between the cotyledons and the root. Therefore, it can be considered a transition zone between shoot and root.

Iron Deficiency Chlorosis. Iron deficiency chlorosis (IDC) is a yellowing of the leaves caused by a lack of iron in the soybean plant. Iron is essential in the formation of chlorophyll, which gives plants their green color. In high pH soils iron becomes insoluble and cannot be absorbed by plant roots. Soybean cultivars differ in their genetic ability to utilize the available iron. A score of 9 means no stunting of the plants or yellowing of the leaves and a score of 1 indicates the plants are dead or dying caused by iron deficiency, a score of 5 means plants have intermediate health with some leaf yellowing.

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Linoleic Acid Percent. Linoleic acid is one of the five most abundant fatty acids in soybean seeds. It is measured by gas chromatography and is reported as a percent of the total oil content.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism, and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Lodging Resistance. Lodging is rated on a scale of 1 to 9. A score of 9 indicates erect plants. A score of 5 indicates plants are leaning at a 45° angle in relation to the ground and a score of 1 indicates plants are lying on the ground.

Maturity Date. Plants are considered mature when 95% of the pods have reached their mature color. The number of days are calculated either from August 31 or from the planting date.

Maturity Group. This refers to an agreed-on industry division of groups of varieties based on zones in which they are adapted, primarily according to day length or latitude. They consist of very long day length varieties (Groups 000, 00, 0), and extend to very short day length varieties (Groups VII, VIII, IX, X).

Relative Maturity (RM). The term relative maturity is a numerical value that is assigned to a soybean variety based on comparisons with the maturity values of other varieties. The number preceding the decimal point in the RM refers to the maturity group. The number following the decimal point refers to the relative earliness or lateness within each maturity group. For example, a 3.0 is an early group III variety, while a 3.9 is a late group III variety.

Oil or Oil Percent. Soybean seeds contain a considerable amount of oil. Oil is measured by NIR spectrophotometry and is reported as a percentage basis.

Oleic Acid Percent. Oleic acid is one of the five most abundant fatty acids in soybean seeds. It is measured by gas chromatography and is reported as a percent of the total oil content.

Palmitic Acid Percent. Palmitic acid is one of the five most abundant fatty acids in soybean seeds. It is measured by gas chromatography and is reported as a percent of the total oil content.

Pedigree Distance. Relationship among generations based on their ancestral links as evidenced in pedigrees. May be measured by the distance of the pedigree from a given starting point in the ancestry.

Percent Identity. Percent identity as used herein refers to the comparison of the homozygous alleles of two soybean varieties. Percent identity is determined by comparing a statistically significant number of the homozygous alleles of two developed varieties. For example, a percent identity of 90% between soybean variety 1 and soybean variety 2 means that the two varieties have the same allele at 90% of their loci.

Percent Similarity. Percent similarity as used herein refers to the comparison of the homozygous alleles of a soybean variety such as soybean cultivar 3317361 with another plant, and if the homozygous allele of soybean cultivar 3317361 matches at least one of the alleles from the other plant, then they are scored as similar. Percent similarity is determined by comparing a statistically significant number of loci and recording the number of loci with similar alleles as a percentage. A percent similarity of 90% between soybean cultivar 3317361 and another plant means that soybean cultivar 3317361 matches at least one of the alleles of the other plant at 90% of the loci.

Phytophthora Tolerance. Tolerance to Phytophthora root rot is rated on a scale of 1 to 9, with a score of 9 being the best or highest tolerance ranging down to a score of 1 which indicates the plants have no tolerance to Phytophthora.

Phenotypic Score. The Phenotypic Score is a visual rating of general appearance of the variety. All visual traits are considered in the score including healthiness, standability, appearance, and freedom of disease. Ratings are scored from 1 being poor to 9 being excellent.

Plant. As used herein, the term "plant" includes reference to an immature or mature whole plant, including a plant from which seed, grain, or anthers have been removed. Seed or embryo that will produce the plant is also considered to be the plant.

Plant Height. Plant height is taken from the top of the soil to the top node of the plant and is measured in centimeters.

Plant Parts. As used herein, the term "plant parts" (or a soybean plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Pod. This refers to the fruit of a soybean plant. It consists of the hull or shell (pericarp) and the soybean seeds.

Progeny. As used herein, includes an $F_1$ soybean plant produced from the cross of two soybean plants where at least one plant includes soybean cultivar 3317361 and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

Protein Percent. Soybean seeds contain a considerable amount of protein. Protein is generally measured by NIR spectrophotometry and is reported on an as is percentage basis.

Pubescence. This refers to a covering of very fine hairs closely arranged on the leaves, stems, and pods of the soybean plant.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Seed Protein Peroxidase Activity. Seed protein peroxidase activity refers to a chemical taxonomic technique to separate cultivars based on the presence or absence of the peroxidase enzyme in the seed coat. There are two types of soybean cultivars; those having high peroxidase activity (dark red color) and those having low peroxidase activity (no color).

Seed Yield (Bushels/Acre). The yield in bushels/acre is the actual yield of the grain at harvest.

Seeds Per Pound. Soybean seeds vary in seed size; therefore, the number of seeds required to make up one pound also varies. The number of seeds per pound affect the pounds of seed required to plant a given area and can also impact end uses.

Shattering. The amount of pod dehiscence prior to harvest. Pod dehiscence involves seeds falling from the pods to the soil. This is a visual score from 1 to 9 comparing all genotypes within a given test. A score of 9 means pods have not opened and no seeds have fallen out. A score of 5 indicates approximately 50% of the pods have opened, with seeds falling to the ground, and a score of 1 indicates 100% of the pods are opened.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

DETAILED DESCRIPTION OF THE INVENTION

Soybean cultivar 3317361 is a late-maturity group V variety. Soybean cultivar 3317361 has very high yield potential when compared to lines of similar maturity and has excellent agronomic characteristics.

Some of the selection criteria used for various generations include: seed yield, lodging resistance, emergence, disease tolerance, maturity, late season plant intactness, plant height, and shattering resistance.

The cultivar has shown uniformity and stability, as described in the following variety description information. It has been self-pollinated a sufficient number of generations with careful attention to uniformity of plant type. The line has been increased with continued observation for uniformity.

Soybean cultivar 3317361 has the following morphologic and other characteristics (based primarily on data collected at DeWitt, Ark.).

TABLE 1

VARIETY DESCRIPTION INFORMATION

Seed Coat Color: Yellow
Seed Coat Luster: Dull
Seed Shape: Spherical flattened
Cotyledon Color: Yellow
Hypocotyl Color: Purple
Leaflet Shape: Ovate
Leaflet Size: Medium
Leaf Color: Medium green
Plant Types: Intermediate
Plant Habit: Determinate
Flower Color: Purple
Hilum Color: Black
Plant Pubescence Color: Tawny
Pod Color: Tan
Maturity Group: V
Relative Maturity: 5.7
Plant Lodging Score (1 = all plants erect; 5 = all plants down badly): 1.7
Plant Height (cm): 90 cm
Seed Size: 16.6 grams per 100 seeds
Reactions to Bacterial Diseases:

Bacterial Pustule: Resistant
Bacterial Blight: Resistant
Wildfire (Pseudomonas syringae pv. tabaci): Resistant
Reactions to Fungal Diseases:

Brown Spot: Not tested but none seen yet
Frogeye Leaf Spot (common to Arkansas) (1 = not having any spots on the leaf; 9 = being totally covered): 1.1 (Resistant)
Stem Canker (southern): Resistant
Pod and Stem Blight: Susceptible
Purple Seed Stain: Moderate
Rhizoctonia Root Rot: Susceptible
Phytophthora Rot:   Race 1: Resistant
                    Race 17: Susceptible
Reactions to Viral Diseases: Seed Mottle (Soybean Mosaic Virus): Resistant AR 2005

TABLE 1-continued

VARIETY DESCRIPTION INFORMATION

Reactions to Nematode Diseases:

Soybean Cyst Nematode Race 3 (HG 0): Resistant
Southern Root Knot Nematode: Moderate
Sudden Death Syndrome (0 = no leaf symptoms; 9 = all plants in plot are affected on all leaves): 5.0 field rating
Physiological Responses:

Iron Chlorosis on Calcareous Soil (1 = no yellowing or stunting, perfectly healthy; 10 = all plants yellow and stunted and/or dying): 8 (Sensitive)
Sodium Chloride (salt tolerance): Excluder This invention is also directed to methods for producing a soybean plant by crossing a first parent soybean plant with a second parent soybean plant, wherein the first or second soybean plant is the soybean plant from cultivar 3317361. Further, both first and second parent soybean plants may be from cultivar 3317361. Therefore, any methods using soybean cultivar 3317361 are part of this invention: selfing, backcrosses, hybrid breeding, and crosses to populations. Any plants produced using soybean cultivar 3317361 as at least one parent are within the scope of this invention.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the invention are intended to be within the scope of this invention.

Further Embodiments of the Invention

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are introduced into the genome using transformation or various breeding methods are referred to herein collectively as "transgenes." In some embodiments of the invention, a transgenic variant of soybean cultivar 3317361 may contain at least one transgene but could contain at least 1, 2, 3, 4, 5, 6, 7, 8, 9, 10, and/or no more than 15, 14, 13, 12, 11, 10, 9, 8, 7, 6, 5, 4, 3, or 2. Over the last fifteen to twenty years several methods for producing transgenic plants have been developed, and the present invention also relates to transgenic variants of the claimed soybean variety 3317361.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6 methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

One embodiment of the invention is a process for producing soybean variety 3317361 further comprising a desired trait, said process comprising introducing a transgene that confers a desired trait to a soybean plant of variety 3317361. Another embodiment is the product produced by this process. In one embodiment the desired trait may be one or more of herbicide resistance, insect resistance, disease resistance, decreased phytate, or modified fatty acid or carbohydrate metabolism. The specific gene may be any known in the art or listed herein, including: a polynucleotide conferring resistance to imidazolinone, dicamba, sulfonylurea, glyphosate, glufosinate, triazine, benzonitrile, cyclohexanedione, phenoxy proprionic acid, and L-phosphinothricin; a polynucleotide encoding a *Bacillus thuringiensis* polypeptide; a polynucleotide encoding phytase, FAD-2, FAD-3, galactinol synthase, or a raffinose synthetic enzyme; or a polynucleotide conferring resistance to soybean cyst nematode, brown stem rot, *Phytophthora* root rot, soybean mosaic virus, or sudden death syndrome.

Numerous methods for plant transformation have been developed, including biological and physical plant transformation protocols. See, for example, Mild et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993), and Armstrong, "The First Decade of Maize Transformation: A Review and Future Perspective," *Maydica*, 44:101-109 (1999). In addition, expression vectors and in vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

A genetic trait which has been engineered into the genome of a particular soybean plant may then be moved into the genome of another variety using traditional breeding techniques that are well known in the plant breeding arts. For example, a backcrossing approach is commonly used to move a transgene from a transformed soybean variety into an already developed soybean variety, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed soybean plants using transformation methods as described below to incorporate transgenes into the genetic material of the soybean plant(s).

Expression Vectors for Soybean Transformation: Marker Genes

Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley, et al., *Proc. Natl. Acad. Sci. USA,* 80:4803 (1983). Another commonly used selectable marker gene is the hygromycin phosphotransferase gene which confers resistance to the antibiotic hygromycin. Vanden Elzen, et al., *Plant Mol. Biol.,* 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford, et al., *Plant Physiol.,* 86:1216 (1988); Jones, et al., *Mol. Gen. Genet.,* 210:86 (1987); Svab, et al., *Plant Mol. Biol.,* 14:197 (1990); Hille, et al., *Plant Mol. Biol.,* 7:171 (1986)). Other selectable marker genes confer resistance to herbicides such as glyphosate, glufosinate, or bromoxynil (Comai, et al., *Nature,* 317:741-744 (1985); Gordon-Kamm, et al., *Plant Cell,* 2:603-618 (1990); Stalker, et al., *Science,* 242:419-423 (1988)).

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.,* 13:67 (1987); Shah, et al., *Science,* 233:478 (1986); Charest, et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri, et al., *EMBO J.,* 8:343 (1989); Koncz, et al., *Proc. Natl. Acad. Sci. USA,* 84:131 (1987); DeBlock, et al., *EMBO J.,* 3:1681 (1984)).

In vivo methods for visualizing GUS activity that do not require destruction of plant tissue are available (Molecular Probes, Publication 2908, IMAGENE GREEN, pp. 1-4 (1993); Naleway, et al., *J. Cell Biol.,* 115:151a (1991)). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells (Chalfie, et al., *Science,* 263:802 (1994)). GFP and mutants of GFP may be used as screenable markers.

Expression Vectors for soybean Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters—An inducible promoter is operably linked to a gene for expression in soybean. Optionally, the inducible promoter is operably linked to a nucleotide sequence encoding a signal sequence which is operably linked to a gene for expression in soybean. With an inducible promoter the rate of transcription increases in response to an inducing agent.

Any inducible promoter can be used in the instant invention. See, Ward, et al., *Plant Mol. Biol.,* 22:361-366 (1993). Exemplary inducible promoters include, but are not limited to, that from the ACEI system which responds to copper (Mett, et al., *Proc. Mid Acad. Sci. USA,* 90:4567-4571 (1993)); In2 gene from maize which responds to benzenesulfonamide herbicide safeners (Hershey, et al., *Mol. Gen. Genetics,* 227:229-237 (1991); Gatz, et al., *Mol. Gen. Genetics,* 243:32-38 (1994)); or Tet repressor from Tn10 (Gatz, et al., *Mol. Gen. Genetics,* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., *Proc. Natl. Acad. Sci. USA,* 88:0421 (1991)).

B. Constitutive Promoters—A constitutive promoter is operably linked to a gene for expression in soybean or the constitutive promoter is operably linked to a nucleotide sequence encoding a signal sequence which is operably linked to a gene for expression in soybean.

Many different constitutive promoters can be utilized in the instant invention. Exemplary constitutive promoters include, but are not limited to, the promoters from plant viruses such as the 35S promoter from CaMV (Odell, et al., *Nature*, 313:810-812 (1985)) and the promoters from such genes as rice actin (McElroy, et al., *Plant Cell*, 2: 163-171 (1990)); ubiquitin (Christensen, et al., *Plant Mol. Biol.*, 12:619-632 (1989); Christensen, et al., *Plant Mol. Biol.*, 18:675-689 (1992)); pEMU (Last, et al., *Theor. Appl. Genet.*, 81:581-588 (1991)); MAS (Velten, et al., *EMBO J.*, 3:2723-2730 (1984)); and maize H3 histone (Lepetit, et al., *Mol. Gen. Genetics*, 231: 276-285 (1992); Atanassova, et al., *Plant Journal*, 2 (3): 291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See, PCT Application WO 96/30530.

C. Tissue-Specific or Tissue-Preferred Promoters—A tissue-specific promoter is operably linked to a gene for expression in soybean. Optionally, the tissue-specific promoter is operably linked to a nucleotide sequence encoding a signal sequence which is operably linked to a gene for expression in soybean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai, et al., *Science*, 23:476-482 (1983); Sengupta-Gopalan, et al., *Proc. Natl. Acad. Sci. USA*, 82:3320-3324 (1985)); a leaf-specific and light-induced promoter such as that from cab or rubisco (Simpson, et al., *EMBO J.*, 4(11): 2723-2729 (1985); Timko, et al., *Nature*, 318:579-582 (1985)); an anther-specific promoter such as that from LAT52 (Twell, et al., *Mol. Gen. Genetics*, 217:240-245 (1989)); a pollen-specific promoter such as that from Zm13 (Guerrero, et al., *Mol. Gen. Genetics*, 244:161-168 (1993)); or a microspore-preferred promoter such as that from apg (Twell, et al., *Sex. Plant Reprod.*, 6:217-224 (1993)).

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.*, 20:49 (1992); Knox, C., et al., *Plant Mol. Biol.*, 9:3-17 (1987); Lerner, et al., *Plant Physiol.*, 91:124-129 (1989); Frontes, et al., *Plant Cell*, 3:483-496 (1991); Matsuoka, et al., *Proc. Natl. Acad. Sci.*, 88:834 (1991); Gould, et al., *J. Cell. Biol.*, 108:1657 (1989); Creissen, et al., *Plant J.*, 2:129 (1991); Kalderon, et al., *Cell*, 39:499-509 (1984); Steifel, et al., *Plant Cell*, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, *Anal. Biochem.*, 114:92-6 (1981).

According to a preferred embodiment, the transgenic plant provided for commercial production of foreign protein is a soybean plant. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, *Methods in Plant Molecular Biology and Biotechnology*, CRC Press, Inc., Boca Raton, 269:284 (1993). Map information concerning chromosomal location is useful for proprietary protection of a subject transgenic plant.

Wang, et al. discuss "Large Scale Identification, Mapping and Genotyping of Single-Nucleotide Polymorphisms in the Human Genome," *Science*, 280:1077-1082 (1998), and similar capabilities are becoming increasingly available for the soybean genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR, and sequencing, all of which are conventional techniques. SNPs may also be used alone or in combination with other techniques.

Likewise, by means of the present invention, plants can be genetically engineered to express various phenotypes of agronomic interest. Through the transformation of soybean, the expression of genes can be altered to enhance disease resistance, insect resistance, herbicide resistance, agronomic, grain quality, and other traits. Transformation can also be used to insert DNA sequences which control or help control male-sterility. DNA sequences native to soybean, as well as non-native DNA sequences, can be transformed into soybean and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT, Lox, or other site specific integration site, antisense technology (see, e.g., Sheehy, et al., *PNAS USA*, 85:8805-8809 (1988); and U.S. Pat. Nos. 5,107,065, 5,453,566, and 5,759,829); co-suppression (e.g., Taylor, *Plant Cell*, 9:1245 (1997); Jorgensen, *Trends Biotech.*, 8(12):340-344 (1990); Flavell, *PNAS USA*, 91:3490-3496 (1994); Finnegan, et al., *Bio/Technology*, 12:883-888 (1994); Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); Montgomery, et al., *PNAS USA*, 95:15502-15507 (1998)), virus-induced gene silencing (Burton, et al., *Plant Cell*, 12:691-705 (2000); Baulcombe, *Curr.*

Op. Plant Bio., 2:109-113 (1999)); target-RNA-specific ribozymes (Haseloff, et al., Nature, 334: 585-591 (1988)); hairpin structures (Smith, et al., Nature, 407:319-320 (2000); WO 99/53050; WO 98/53083); MicroRNA (Aukerman & Sakai, Plant Cell, 15:2730-2741 (2003)); ribozymes (Steinecke, et al., EMBO J., 11:1525 (1992); Perriman, et al., Antisense Res. Dev., 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example, Jones, et al., Science, 266:789 (1994) (cloning of the tomato Cf-9 gene for resistance to Cladosporium fulvum); Martin, et al., Science, 262:1432 (1993) (tomato Pto gene for resistance to Pseudomonas syringae pv. tomato encodes a protein kinase); Mindrinos, et al., Cell, 78:1089 (1994) (Arabidopsis RSP2 gene for resistance to Pseudomonas syringae); McDowell & Woffenden, Trends Biotechnol., 21(4):178-83 (2003); and Toyoda, et al., Transgenic Res., 11 (6):567-82 (2002).

B. A gene conferring resistance to a pest, such as soybean cyst nematode. See, e.g., PCT Application WO 96/30517 and PCT Application WO 93/19181.

C. A Bacillus thuringiensis protein, a derivative thereof or a synthetic polypeptide modeled thereon. See, for example, Geiser, et al., Gene, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

D. A lectin. See, for example, Van Damme, et al., Plant Molec. Biol., 24:25 (1994), who disclose the nucleotide sequences of several Clivia miniata mannose-binding lectin genes.

E. A vitamin-binding protein such as avidin. See, PCT Application US 93/06487, which teaches the use of avidin and avidin homologues as larvicides against insect pests.

F. An enzyme inhibitor, for example, a protease or proteinase inhibitor or an amylase inhibitor. See, for example, Abe, et al., J. Biol. Chem., 262:16793 (1987) (nucleotide sequence of rice cysteine proteinase inhibitor); Huub, et al., Plant Molec. Biol., 21:985 (1993) (nucleotide sequence of cDNA encoding tobacco proteinase inhibitor I); Sumitani, et al., Biosci. Biotech. Biochem., 57:1243 (1993) (nucleotide sequence of Streptomyces nitrosporeus α-amylase inhibitor); and U.S. Pat. No. 5,494,813 (Hepher and Atkinson, issued Feb. 27, 1996).

G. An insect-specific hormone or pheromone, such as an ecdysteroid or juvenile hormone, a variant thereof, a mimetic based thereon, or an antagonist or agonist thereof. See, for example, the disclosure by Hammock, et al., Nature, 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor); Pratt, et al., Biochem. Biophys. Res. Comm., 163:1243 (1989) (an allostatin is identified in Diploptera puntata); Chattopadhyay, et al., Critical Reviews in Microbiology, 30(1):33-54 (2004); Zjawiony, J Nat Prod, 67(2):300-310 (2004); Carlini & Grossi-de-Sa, Toxicon, 40(11):1515-1539 (2002); Ussuf, et al., Curr Sci., 80(7):847-853 (2001); Vasconcelos & Oliveira, Toxicon, 44(4):385-403 (2004). See also, U.S. Pat. No. 5,266,317 to Tomalski, et al., which discloses genes encoding insect-specific, paralytic neurotoxins.

I. An insect-specific venom produced in nature by a snake, a wasp, etc. For example, see, Pang, et al., Gene, 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative, or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott, et al.), which discloses the nucleotide sequence of a callase gene. DNA molecules which contain chitinase-encoding sequences can be obtained, for example, from the ATCC under Accession Nos. 39637 and 67152. See also, Kramer, et al., Insect Biochem. Molec. Biol., 23:691 (1993), who teach the nucleotide sequence of a cDNA encoding tobacco hornworm chitinase, and Kawalleck, et al., Plant Molec. Biol., 21:673 (1993), who provide the nucleotide sequence of the parsley ubi4-2 polyubiquitin gene, U.S. Pat. Nos. 7,145,060, 7,087,810, and 6,563,020.

L. A molecule that stimulates signal transduction. For example, see the disclosure by Botella, et al., Plant Molec. Biol., 24:757 (1994), of nucleotide sequences for mung bean calmodulin cDNA clones, and Griess, et al., Plant Physiol., 104:1467 (1994), who provide the nucleotide sequence of a maize calmodulin cDNA clone.

M. A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

N. A membrane permease, a channel former or a channel blocker. For example, see the disclosure of Jaynes, et al., Plant Sci, 89:43 (1993), of heterologous expression of a cecropin-β lytic peptide analog to render transgenic tobacco plants resistant to Pseudomonas solanacearum.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., Ann. Rev. Phytopathol., 28:451 (1990). Coat protein-mediated resistance has been conferred upon transformed plants against alfalfa mosaic virus, cucumber mosaic virus, and tobacco mosaic virus.

P. An insect-specific antibody or an immunotoxin derived therefrom. Thus, an antibody targeted to a critical metabolic function in the insect gut would inactivate an affected enzyme, killing the insect. See, Taylor, et al., Abstract #497, Seventh Int'l Symposium on Molecular Plant-Microbe Interactions (Edinburgh, Scotland 1994) (enzymatic inactivation in transgenic tobacco via production of single-chain antibody fragments).

Q. A virus-specific antibody. See, for example, Tavladoraki, et al., *Nature*, 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, Lamb, et al., *Bio/Technology*, 10:1436 (1992). The cloning and characterization of a gene which encodes a bean endopolygalacturonase-inhibiting protein is described by Toubart, et al., *Plant J.*, 2:367 (1992).

S. A developmental-arrestive protein produced in nature by a plant. For example, Logemann, et al., *Bio/Technology*, 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology*, 5(2) (1995); Pieterse & Van Loon, *Curr. Opin. Plant Bio.*, 7(4):456-64 (2004); and Somssich, *Cell*, 113(7):815-6 (2003).

U. Antifungal genes. See, Cornelissen and Melchers, *Plant Physiol.*, 101:709-712 (1993); Parijs, et al., *Planta*, 183:258-264 (1991); and Bushnell, et al., *Can. J. of Plant Path.*, 20(2): 137-149 (1998). See also, U.S. Pat. No. 6,875,907.

V. Detoxification genes, such as for fumonisin, beauvericin, moniliformin, and zearalenone and their structurally-related derivatives. See, for example, U.S. Pat. No. 5,792,931.

W. Cystatin and cysteine proteinase inhibitors. See, U.S. Pat. No. 7,205,453.

X. Defensin genes. See, WO 03/000863 and U.S. Pat. No. 6,911,577.

Y. Genes conferring resistance to nematodes, and in particular soybean cyst nematodes. See, e.g., PCT Applications WO 96/30517, WO 93/19181, and WO 03/033651; Urwin, et al., *Planta*, 204:472-479 (1998); Williamson, *Curr Opin Plant Bio.*, 2(4):327-31 (1999).

Z. Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7, and other Rps genes. See, for example, Shoemaker, et al., *Phytophthora* Root Rot Resistance Gene Mapping in Soybean, Plant Genome IV Conference, San Diego, Calif. (1995).

AA. Genes that confer resistance to Brown Stem Rot, such as described in U.S. Pat. No. 5,689,035 and incorporated by reference for this purpose.

Any of the above-listed disease or pest resistance genes (A-AA) can be introduced into the claimed soybean cultivar through a variety of means including, but not limited to, transformation and crossing.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee, et al., *EMBO J.*, 7:1241 (1988) and Miki, et al., *Theor. Appl. Genet.*, 80:449 (1990), respectively.

B. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT) and *Streptomyces hygroscopicus* PAT bar genes), pyridinoxy or phenoxy proprionic acids, and cyclohexanediones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587, 6,338,961, 6,248,876, 6,040,497, 5,804, 425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, RE 36,449, RE 37,287, and U.S. Pat. No. 5,491,288; and International Publications EP1173580, WO 01/66704, EP1173581, and EP1173582, which are incorporated herein by reference for this purpose. Glyphosate resistance is also imparted to plants that express a gene that encodes a glyphosate oxido-reductase enzyme, as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. application Ser. No. 10/427,692. A DNA molecule encoding a mutant aroA gene can be obtained under ATCC Accession No. 39256, and the nucleotide sequence of the mutant gene is disclosed in U.S. Pat. No. 4,769,061 to Comai. European Patent Appl. No. 0 333 033 to Kumada, et al. and U.S. Pat. No. 4,975,374 to Goodman, et al., disclose nucleotide sequences of glutamine synthetase genes which confer resistance to herbicides such as L-phosphinothricin. The nucleotide sequence of a PAT gene is provided in European Patent Appl. No. 0 242 246 to Leemans, et al. DeGreef, et al., *Bio/Technology*, 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall, et al., *Theor. Appl. Genet.*, 83:435 (1992).

C. An herbicide that inhibits photosynthesis, such as a triazine (psbA and gs+genes) and a benzonitrile (nitrilase gene). Przibila, et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes, et al., *Biochem. J.*, 285:173 (1992).

D. Acetohydroxy acid synthase, which has been found to make plants that express this enzyme resistant to multiple types of herbicides, has been introduced into a variety of plants. See, Hattori, et al., *Mol. Gen. Genet.*, 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.*, 106:17 (1994)); genes for glutathione reductase and superoxide dismutase (Aono, et al., *Plant Cell Physiol.*, 36:1687 (1995)); and genes for various phosphotransferases (Datta, et al., *Plant Mol. Biol.*, 20:619 (1992)).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767, 373, and International Publication WO 01/12825.

Any of the above listed herbicide genes (A-E) can be introduced into the claimed soybean cultivar through a variety of means including but not limited to transformation and crossing.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See, Knultzon, et al., *Proc. Natl. Acad. Sci. USA*, 89:2625 (1992).

B. Decreased phytate content: 1) Introduction of a phytase-encoding gene enhances breakdown of phytate, adding more free phosphate to the transformed plant. For example, see, Van Hartingsveldt, et al., *Gene*, 127:87 (1993), for a disclosure of the nucleotide sequence of an *Aspergillus niger* phytase gene. 2) Up-regulation of a gene that reduces phytate content. In maize, this, for example, could be accomplished by cloning and then re-introducing DNA associated with one or more of the alleles, such as the LPA alleles, identified in maize mutants characterized by low levels of phytic acid, such as in Raboy, et al., *Maydica*, 35:383 (1990), and/or by altering inositol kinase activity as in WO 02/059324, U.S. Publ. No. 2003/000901, WO 03/027243, U.S. Publ. No. 2003/0079247, WO 99/05298, U.S. Pat. No. 6,197,561, U.S. Pat. No. 6,291,224, U.S. Pat. No. 6,391,348, WO 2002/059324, U.S. Publ. No. 2003/0079247, WO 98/45448, W 099/55882, and WO 01/04147.

C. Modified carbohydrate composition effected, for example, by transforming plants with a gene coding for an enzyme that alters the branching pattern of starch, or a gene altering thioredoxin, such as NTR and/or TRX (see, U.S. Pat. No. 6,531,648, which is incorporated by reference for this purpose), and/or a gamma zein knock out or mutant, such as cs27 or TUSC27 or en27 (see, U.S. Pat. No. 6,858,778, and U.S. Publ. Nos. 2005/0160488 and 2005/0204418, which are incorporated by reference for this purpose). See, Shiroza, et al., *J. Bacteriol.*, 170:810 (1988) (nucleotide sequence of *Streptococcus mutans* fructosyltransferase gene); Steinmetz, et al., *Mol. Gen. Genet.*, 200:220 (1985) (nucleotide sequence of *Bacillus subtilis* levansucrase gene); Pen, et al., *Bio/Technology*, 10:292 (1992) (production of transgenic plants that express *Bacillus licheniformis* alpha-amylase); Elliot, et al., *Plant Molec. Biol.*, 21:515 (1993) (nucleotide sequences of tomato invertase genes); Sogaard, et al., *J. Biol. Chem.*, 268: 22480 (1993) (site-directed mutagenesis of barley alpha-amylase gene); Fisher, et al., *Plant Physiol.*, 102:1045 (1993) (maize endosperm starch branching enzyme II); WO 99/10498 (improved digestibility and/or starch extraction through modification of UDP-D-xylose 4-epimerase, Fragile 1 and 2, Ref 1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

D. Elevated oleic acid via FAD-2 gene modification and/or decreased linolenic acid via FAD-3 gene modification. See, U.S. Pat. Nos. 6,063,947, 6,323,392, and International Publication WO 93/11245. Linolenic acid is one of the five most abundant fatty acids in soybean seeds. The low oxidative stability of linolenic acid is one reason that soybean oil undergoes partial hydrogenation. When partially hydrogenated, all unsaturated fatty acids form trans fats. Soybeans are the largest source of edible-oils in the U.S. and 40% of soybean oil production is partially hydrogenated. The consumption of trans fats increases the risk of heart disease. Regulations banning trans fats have encouraged the development of low linolenic soybeans. Soybeans containing low linolenic acid percentages create a more stable oil requiring hydrogenation less often. This provides trans fat free alternatives in products such as cooking oil.

E. Altering conjugated linolenic or linoleic acid content, such as in WO 01/12800. Altering LEC1, AGP, Dek1, Superal1, milps, and various Ipa genes, such as Ipa1, Ipa3, hpt, or hggt. See, for example, WO 02/42424, WO 98/22604, WO 03/011015, WO 02/057439, WO 03/011015, U.S. Pat. Nos. 6,423,886, 6,197,561, 6,825,397, 7,157,621, U.S. Publ. No. 2003/0079247, and Rivera-Madrid, R., et al., *Proc. Natl. Acad. Sci.*, 92:5620-5624 (1995).

F. Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

G. Altered essential seed amino acids. See, for example, U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 (high lysine); U.S. Pat. No. 5,850,016 (alteration of amino acid compositions in seeds); U.S. Pat. No. 5,885,802 (high methionine); U.S. Pat. No. 5,885,801 (high threonine); U.S. Pat. No. 6,664, 445 (plant amino acid biosynthetic enzymes); U.S. Pat. No. 6,459,019 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); U.S. Pat. No. 5,633,436 (increasing sulfur amino acid content); U.S. Pat. No. 5,559,223 (synthetic storage proteins with defined structure containing programmable levels of essential amino acids for improvement of the nutritional value of plants); U.S. Pat. No. 6,194,638 (hemicellulose); U.S. Pat. No. 7,098,381 (UDPGdH); U.S. Pat. No. 6,194,638 (RGP); U.S. Pat. Nos. 6,399,859, 6,930,225, 7,179,955, and 6,803,498; U.S. Publ. No. 2004/0068767; WO 99/40209 (alteration of amino acid compositions in seeds); WO 99/29882 (methods for altering amino acid content of proteins); WO 98/20133 (proteins with enhanced levels of essential amino acids); WO 98/56935 (plant amino acid biosynthetic enzymes); WO 98/45458 (engineered seed protein having higher percentage of essential amino acids); WO 98/42831 (increased lysine); WO 96/01905 (increased threonine); WO 95/15392 (increased lysine); WO 01/79516; and WO 00/09706 (Ces A: cellulose synthase).

4. Genes that Control Male Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describes a system of nuclear male sterility which includes:

identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. Introduction of a deacetylase gene under the control of a tapetum-specific promoter and with the application of the chemical N-Ac-PPT. See, International Publication WO 01/29237.

B. Introduction of various stamen-specific promoters. See, International Publications WO 92/13956 and WO 92/13957.

C. Introduction of the barnase and the barstar genes. See, Paul, et al., *Plant Mol. Biol.*, 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640, all of which are hereby incorporated by reference.

5. Genes that Create a Site for Site Specific DNA Integration:

This includes the introduction of FRT sites that may be used in the FLP/FRT system and/or Lox sites that may be used in the Cre/Loxp system. See, for example, Lyznik, et al., Site-Specific Recombination for Genetic Engineering in Plants, *Plant Cell Rep*, 21:925-932 (2003) and WO 99/25821, which are hereby incorporated by reference. Other systems that may be used include the Gin recombinase of phage Mu (Maeser, et al. (1991); Vicki Chandler, The Maize Handbook, Ch. 118 (Springer-Verlag 1994)); the Pin recombinase of *E. coli* (Enomoto, et al. (1983)); and the R/RS system of the pSR1 plasmid (Araki, et al. (1992)).

6. Genes that Affect Abiotic Stress Resistance:

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. application Ser. No. 10/817,483, and U.S. Pat. No. 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. Nos. 6,573,430 (TFL), 6,713,663 (FT), 6,794,560, 6,307,126 (GAI), WO 96/14414 (CON), WO 96/38560, WO 01/21822 (VRN1), WO 00/44918 (VRN2), WO 99/49064 (GI), WO 00/46358 (FR1), WO 97/29123, WO 99/09174 (D8 and Rht), WO 2004/076638, and WO 004/031349 (transcription factors).

Methods for Soybean Transformation

Numerous methods for plant transformation have been developed including biological and physical plant transformation protocols. See, for example, Miki, et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium*. See, for example, Horsch, et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Reports*, 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford, et al., *Part. Sci. Technol.*, 5:27 (1987); Sanford, J. C., *Trends Biotech.*, 6:299 (1988); Klein, et al., *Bio/Tech.*, 6:559-563 (1988); Sanford, J. C., *Physiol Plant*, 7:206 (1990); Klein, et al., *Biotechnology*, 10:268 (1992). See also, U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang, et al., *Bio/Technology*, 9:996 (1991). Alternatively, liposome and spheroplast fusion have been used to introduce expression vectors into plants. Deshayes, et al., *EMBO J.*, 4:2731 (1985); Christou, et al., *Proc Natl. Acad. Sci. USA*, 84:3962 (1987). Direct uptake of DNA into protoplasts using $CaCl_2$ precipitation, polyvinyl alcohol or poly-L-ornithine have also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described (Donn, et al., In Abstracts of VIIth International Congress on Plant Cell and Tissue Culture IAPTC, A2-38, p. 53 (1990); D'Halluin, et al., *Plant Cell,* 4:1495-1505 (1992); and Spencer, et al., *Plant Mol. Biol.,* 24:51-61 (1994)).

Following transformation of soybean target tissues, expression of the above-described selectable marker genes allows for preferential selection of transformed cells, tissues, and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular soybean line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Genetic Marker Profile Through SSR and First Generation Progeny

In addition to phenotypic observations, a plant can also be identified by its genotype. The genotype of a plant can be characterized through a genetic marker profile which can identify plants of the same variety, or a related variety, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs). For example, see, Cregan, et al., "An Integrated Genetic Linkage Map of the Soybean Genome," *Crop Science,* 39:1464-1490 (1999) and Berry, et al., "Assessing Probability of Ancestry Using Simple Sequence Repeat Profiles: Applications to Maize Inbred Lines and Soybean Varieties," *Genetics,* 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for soybean cultivar 3317361.

Primers and PCR protocols for assaying these and other markers are disclosed in the Soybase (sponsored by the USDA Agricultural Research Service and Iowa State University). In addition to being used for identification of soybean variety 3317361, and plant parts and plant cells of soybean variety 3317361, the genetic profile may be used to identify a soybean plant produced through the use of soybean cultivar 3317361 or to verify a pedigree for progeny plants produced through the use of soybean cultivar 3317361. The genetic marker profile is also useful in breeding and developing backcross conversions.

The present invention comprises a soybean plant characterized by molecular and physiological data obtained from the representative sample of said variety deposited with the American Type Culture Collection (ATCC). Further provided by the invention is a soybean plant formed by the combination of the disclosed soybean plant or plant cell with another soybean plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Primers used are publicly available and may be found in the Soybase or Cregan supra. See also, PCT Publication No. WO 99/31964 (Nucleotide Polymorphisms in Soybean); U.S. Pat. No. 6,162,967 (Positional Cloning of Soybean Cyst Nematode Resistance Genes); and U.S. application Ser. No. 09/954,773 (Soybean Sudden Death Syndrome Resistant Soybeans and Methods of Breeding and Identifying Resistant Plants), the disclosure of which are incorporated herein by reference.

The SSR profile of soybean plant 3317361 can be used to identify plants comprising soybean cultivar 3317361 as a parent, since such plants will comprise the same homozygous alleles as soybean cultivar 3317361. Because the soybean variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of soybean cultivar 3317361 in their development, such as soybean cultivar 3317361 comprising a backcross conversion, transgene, or genetic sterility factor, may be identified by having a molecular marker profile with a high percent identity to soybean cultivar 3317361. Such a percent identity might be 95%, 96%, 97%, 98%, 99%, 99.5%, or 99.9% identical to soybean cultivar 3317361.

The SSR profile of soybean cultivar 3317361 can also be used to identify essentially derived varieties and other progeny varieties developed from the use of soybean cultivar 3317361, as well as cells and other plant parts thereof. Such plants may be developed using the markers identified in WO 00/31964, U.S. Pat. No. 6,162,967, and U.S. application Ser. No. 09/954,773. Progeny plants and plant parts produced using soybean cultivar 3317361 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from soybean variety, as measured by either percent identity or percent similarity. Such progeny may be further characterized as being within a pedigree distance of soybean cultivar 3317361, such as within 1, 2, 3, 4, or 5 or less cross-pollinations to a soybean plant other than soybean cultivar 3317361 or a plant that has soybean cultivar 3317361 as a progenitor. Unique molecular profiles may be identified with other molecular tools such as SNPs and RFLPs.

While determining the SSR genetic marker profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Single-Gene Conversions

When the term "soybean plant" is used in the context of the present invention, this also includes any single gene conversions of that variety. The term single gene converted plant as used herein refers to those soybean plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental soybean plant that contributes the gene for the desired characteristic is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol (Poehlman & Sleper (1994); Fehr, Principles of Cultivar Development, pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic. Examples of these traits include, but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Several of these single gene traits are described in U.S. Pat. Nos. 5,959,185, 5,973,234, and 5,977,445, the disclosures of which are specifically hereby incorporated by reference.

Introduction of a New Trait or Locus into Soybean Cultivar 3317361

Variety 3317361 represents a new base genetic variety into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of Soybean Cultivar 3317361

A backcross conversion of soybean cultivar 3317361 occurs when DNA sequences are introduced through backcrossing (Hallauer, et al., "Corn Breeding," *Corn and Corn Improvements*, No. 18, pp. 463-481 (1988)), with soybean cultivar 3317361 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, *Proceedings Symposium of the Analysis of Molecular Data*, Crop Science Society of America, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. (See, Hallauer, et al., *Corn and Corn Improvement*, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments of the invention, the number of loci that may be backcrossed into soybean cultivar 3317361 is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, Breeding Field Crops, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in soybean variety 3317361 comprises crossing soybean cultivar 3317361 plants grown from soybean cultivar 3317361 seed with plants of another soybean variety that comprise the desired trait or locus, selecting $F_1$ progeny plants that comprise the desired trait or locus to produce selected $F_1$ progeny plants, crossing the selected progeny plants with the soybean cultivar 3317361 plants to produce backcross progeny plants, selecting for backcross progeny plants that have the desired trait or locus and the morphological characteristics of soybean variety 3317361 to produce selected backcross progeny plants, and backcrossing to soybean cultivar 3317361 three or more times in succession to produce selected fourth or higher backcross progeny plants that comprise said trait or locus. The modified soybean cultivar 3317361 may be further characterized as having the physiological and morphological characteristics of soybean variety 3317361 listed in Table 1 as determined at the 5% significance level when grown in the same environmental conditions and/or may be characterized by percent similarity or identity to soybean cultivar 3317361 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny soybean seed by adding a step at the end of the process that comprises crossing soybean cultivar 3317361 with the introgressed trait or locus with a different soybean plant and harvesting the resultant first generation progeny soybean seed.

Tissue Culture

Further reproduction of the variety can occur by tissue culture and regeneration. Tissue culture of various tissues of soybeans and regeneration of plants therefrom is well known and widely published. For example, reference may be had to Komatsuda, T., et al., *Crop Sci.*, 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992); as well as U.S. Pat. No. 5,024,944, issued Jun. 18, 1991 to Collins, et al. and U.S. Pat. No. 5,008,200, issued Apr. 16, 1991 to Ranch, et al. Thus, another aspect of this invention is to provide cells which upon growth and differentiation produce soybean plants having the physiological and morphological characteristics of soybean cultivar 3317361.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Using Soybean Cultivar 3317361 to Develop Other Soybean Varieties

Soybean varieties such as soybean cultivar 3317361 are typically developed for use in seed and grain production. However, soybean varieties such as soybean cultivar 3317361 also provide a source of breeding material that may be used to develop new soybean varieties. Plant breeding techniques known in the art and used in a soybean plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of soybean varieties in a plant breeding program requires, in general, the development and evaluation of homozygous varieties. There are many analytical methods available to evaluate a new variety. The oldest and most traditional method of analysis is the observation of phenotypic traits, but genotypic analysis may also be used.

Additional Breeding Methods

This invention is directed to methods for producing a soybean plant by crossing a first parent soybean plant with a second parent soybean plant wherein either the first or second parent soybean plant is variety 3317361. The other parent may be any other soybean plant, such as a soybean plant that is part of a synthetic or natural population. Any such methods using soybean variety 3317361 are part of this invention: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can be found in one of several reference books (e.g., Allard, Principles of Plant Breeding (1960); Simmonds, Principles of Crop Improvement (1979); Sneep, et al. (1979); Fehr, "Breeding Methods for Cultivar Development," Chapter 7, Soybean Improvement, Production and Uses, 2.sup.nd ed., Wilcox editor (1987)).

The following describes breeding methods that may be used with soybean cultivar 3317361 in the development of further soybean plants. One such embodiment is a method for developing a cultivar 3317361 progeny soybean plant in a soybean plant breeding program comprising: obtaining the soybean plant, or a part thereof, of cultivar 3317361, utilizing said plant, or plant part, as a source of breeding material, and selecting a soybean cultivar 3317361 progeny plant with molecular markers in common with cultivar 3317361 and/or with morphological and/or physiological characteristics selected from the characteristics listed in Tables 1 or 2. Breeding steps that may be used in the soybean plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of soybean cultivar 3317361 progeny soybean plants, comprising crossing cultivar 3317361 with another soybean plant, thereby producing a population of soybean plants which, on average, derive 50% of their alleles from soybean cultivar 3317361. A plant of this population may be selected and repeatedly selfed or sibbed with a soybean cultivar resulting from these successive filial generations. One embodiment of this invention is the soybean cultivar produced by this method and that has obtained at least 50% of its alleles from soybean cultivar 3317361.

One of ordinary skill in the art of plant breeding would know how to evaluate the traits of two plant varieties to determine if there is no significant difference between the two traits expressed by those varieties. For example, see, Fehr and Walt, *Principles of Cultivar Development, pp.* 261-286 (1987). Thus the invention includes soybean cultivar 3317361 progeny soybean plants comprising a combination of at least two cultivar 3317361 traits selected from the group consisting of those listed in Tables 1 and 2 or the cultivar 3317361 combination of traits listed in the Summary of the Invention, so that said progeny soybean plant is not significantly different for said traits than soybean cultivar 3317361 as determined at the 5% significance level when grown in the same environmental conditions. Using techniques described herein, molecular markers may be used to identify said progeny plant as a soybean cultivar 3317361 progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of soybean cultivar 3317361 may also be characterized through their filial relationship with soybean cultivar 3317361, as for example, being within a certain number of breeding crosses of soybean cultivar 3317361. A breeding cross is a cross made to introduce new genetics into the progeny, and is distinguished from a cross, such as a self or a sib cross, made to select among existing genetic alleles. The lower the number of breeding crosses in the pedigree, the closer the relationship between soybean cultivar 3317361 and its progeny. For example, progeny produced by the methods described herein may be within 1, 2, 3, 4, or 5 breeding crosses of soybean cultivar 3317361.

As used herein, the term "plant" includes plant cells, plant protoplasts, plant cell tissue cultures from which soybean plants can be regenerated, plant calli, plant clumps, and plant cells that are intact in plants or parts of plants, such as embryos, pollen, ovules, flowers, pods, leaves, roots, root tips, anthers, cotyledons, hypocotyls, meristematic cells, stems, pistils, petiole, and the like.

Pedigree Breeding

Pedigree breeding starts with the crossing of two genotypes, such as soybean cultivar 3317361 and another soybean variety having one or more desirable characteristics that is lacking or which complements soybean cultivar 3317361. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a soybean variety may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new soybean varieties.

Therefore, an embodiment of this invention is a method of making a backcross conversion of soybean variety 3317361, comprising the steps of crossing a plant of soybean variety 3317361 with a donor plant comprising a desired trait, selecting an $F_1$ progeny plant comprising the desired trait, and backcrossing the selected $F_1$ progeny plant to a plant of soybean variety 3317361. This method may further comprise the step of obtaining a molecular marker profile of soybean variety 3317361 and using the molecular marker profile to select for a progeny plant with the desired trait and the molecular marker profile of soybean cultivar 3317361. In one embodiment, the desired trait is a mutant gene or transgene present in the donor parent.

Recurrent Selection and Mass Selection

Recurrent selection is a method used in a plant breeding program to improve a population of plants. Soybean cultivar 3317361 is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self pollination, directed pollination could be used as part of the breeding program.

Mutation Breeding

Mutation breeding is another method of introducing new traits into soybean variety 3317361. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, "Principles of Cultivar Development," Macmillan Publishing Company (1993). In addition, mutations created in other soybean plants may be used to produce a backcross conversion of soybean cultivar 3317361 that comprises such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing soybean cultivar 3317361.

Isozyme Electrophoresis and RFLPs have been widely used to determine genetic composition. Shoemaker and Olsen, Molecular Linkage Map of Soybean (*Glycine max* L. Merr.), pp. 6.131-6.138 (1993). In S. J. O'Brien (ed.), *Genetic Maps: Locus Maps of Complex Genomes*, Cold Spring Harbor Laboratory Press, Cold Spring Harbor, N.Y., developed a molecular genetic linkage map that consisted of 25 linkage groups with about 365 RFLP, 11 RAPD (random amplified polymorphic DNA), 3 classical markers, and 4 isozyme loci. See also, Shoemaker, R. C., 1994 RFLP Map of Soybean, pp. 299-309; In R. L. Phillips and I. K. Vasil (ed.), *DNA-based markers in plants*, Kluwer Academic Press Dordrecht, the Netherlands.

SSR technology is currently the most efficient and practical marker technology. More marker loci can be routinely used, and more alleles per marker locus can be found, using SSRs in comparison to RFLPs. For example, Diwan and Cregan described a highly polymorphic microsatellite loci in soybean with as many as 26 alleles. (Diwan, N., and Cregan. P. B., Automated sizing of fluorescent-labeled simple sequence repeat (SSR) markers to assay genetic variation in Soybean, *Theor. Appl. Genet.*, 95:220-225 (1997). Single Nucleotide Polymorphisms may also be used to identify the unique genetic composition of the invention and progeny varieties retaining that unique genetic composition. Various molecular marker techniques may be used in combination to enhance overall resolution.

Soybean DNA molecular marker linkage maps have been rapidly constructed and widely implemented in genetic studies. One such study is described in Cregan, et. al, "An Integrated Genetic Linkage Map of the Soybean Genome," *Crop Science*, 39:1464-1490 (1999). Sequences and PCR conditions of SSR Loci in Soybean, as well as the most current genetic map, may be found in Soybase on the World Wide Web.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a soybean plant for which soybean cultivar 3317361 is a parent can be used to produce double haploid plants. Double haploids are produced by the doubling of a set of chromosomes (1 N) from a heterozygous plant to produce a completely homozygous individual. For example, see, Wan, et al., "Efficient Production of Doubled Haploid Plants Through Colchicine Treatment of Anther-Derived Maize Callus," *Theoretical and Applied Genetics*, 77:889-892 (1989) and U.S. Pat. No. 7,135,615. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, *Am. Nat.*, 93:381-382 (1959); Sharkar and Coe, *Genetics*, 54:453-464 (1966); KEMS (Deimling, Roeber, and Geiger, *Vortr. Pflanzenzuchtg*, 38:203-224 (1997); or KMS and ZMS (Chalyk, Bylich & Chebotar, *MNL*, 68:47 (1994); Chalyk & Chebotar, *Plant Breeding*, 119:363-364 (2000)); and indeterminate gametophyte (ig) mutation (Kermicle, *Science*, 166:1422-1424 (1969). The disclosures of which are incorporated herein by reference.

Methods for obtaining haploid plants are also disclosed in Kobayashi, M., et al., Journ. of Heredity, 71(1):9-14 (1980); Pollacsek, M., Agronomie (Paris) 12(3):247-251 (1992); Cho-Un-Haing, et al., *Journ. of Plant Biol.*, 39(3):185-188 (1996); Verdoodt, L., et al., 96(2):294-300 (February 1998); Genetic Manipulation in Plant Breeding, Proceedings International Symposium Organized by EUCARPIA, Berlin, Germany (Sep. 8-13, 1985); Chalyk, et al., *Maize Genet Coop*., Newsletter 68:47 (1994).

Thus, an embodiment of this invention is a process for making a substantially homozygous soybean cultivar 3317361 progeny plant by producing or obtaining a seed from the cross of soybean cultivar 3317361 and another soybean plant and applying double haploid methods to the $F_1$ seed or $F_1$ plant or to any successive filial generation. Based on studies in maize and currently being conducted in soybean, such methods would decrease the number of generations required to produce a variety with similar genetics or characteristics to soybean cultivar 3317361. See, Bernardo, R. and Kahler, A. L., *Theor. Appl. Genet.*, 102:986-992 (2001).

In particular, a process of making seed retaining the molecular marker profile of soybean variety 3317361 is contemplated, such process comprising obtaining or producing $F_1$ seed for which soybean variety 3317361 is a parent, inducing doubled haploids to create progeny without the occurrence of meiotic segregation, obtaining the molecular marker profile of soybean variety 3317361, and selecting progeny that retain the molecular marker profile of soybean cultivar 3317361.

Descriptions of other breeding methods that are commonly used for different traits and crops can be found in one of several reference books (e.g., Allard (1960); Simmonds (1979); Sneep, et al. (1979); Fehr (1987)).

INDUSTRIAL USES

The seed of soybean cultivar 3317361, the plant produced from the seed, the hybrid soybean plant produced from the crossing of the variety with any other soybean plant, hybrid seed, and various parts of the hybrid soybean plant can be utilized for human food, livestock feed, and as a raw material in industry. The soybean seeds produced by soybean cultivar 3317361 can be crushed, or a component of the soybean seeds can be extracted, in order to comprise a commodity plant product, such as protein concentrate, protein isolate, soybean hulls, meal, flour, or oil for a food or feed product.

The soybean is the world's leading source of vegetable oil and protein meal. The oil extracted from soybeans is used for cooking oil, margarine, and salad dressings. Soybean oil is composed of saturated, monounsaturated, and polyunsaturated fatty acids. It has a typical composition of 11% palmitic, 4% stearic, 25% oleic, 50% linoleic, and 9% linolenic fatty acid content ("Economic Implications of Modified Soybean Traits Summary Report," Iowa Soybean Promotion Board and American Soybean Association Special Report 92S (May 1990)). Changes in fatty acid composition for improved oxidative stability and nutrition are constantly sought after. Industrial uses of soybean oil, which is subjected to further processing, include ingredients for paints, plastics, fibers, detergents, cosmetics, lubricants, and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils to produce the desired type of oil or fat.

Soybean cultivar 3317361 can be used to produce soybean oil. To produce soybean oil, the soybeans harvested from soybean cultivar 3317361 are cracked, adjusted for moisture content, rolled into flakes and the oil is solvent-extracted from the flakes with commercial hexane. The oil is then refined, blended for different applications, and sometimes hydrogenated. Soybean oils, both liquid and partially hydrogenated, are used domestically and exported, sold as "vegetable oil" or are used in a wide variety of processed foods.

Soybeans are also used as a food source for both animals and humans. Soybeans are widely used as a source of protein for poultry, swine, and cattle feed. During processing of whole soybeans, the fibrous hull is removed and the oil is extracted. The remaining soybean meal is a combination of carbohydrates and approximately 50% protein.

Soybean cultivar 3317361 can be used to produce meal. After oil is extracted from whole soybeans harvested from soybean cultivar 3317361, the remaining material or "meal" is "toasted" (a misnomer because the heat treatment is with moist steam) and ground in a hammer mill. Soybean meal is an essential element of the American production method of growing farm animals, such as poultry and swine, on an industrial scale that began in the 1930s; and more recently the aquaculture of catfish. Ninety-eight percent of the U.S. soybean crop is used for livestock feed. Soybean meal is also used in lower end dog foods. Soybean meal produced from soybean cultivar 3317361 can also be used to produce soybean protein concentrate and soybean protein isolate.

In addition to soybean meal, soybean cultivar 3317361 can be used to produce soy flour. Soy flour refers to defatted soybeans where special care was taken during desolventizing (not toasted) to minimize denaturation of the protein and to retain a high Nitrogen Solubility Index (NSI) in making the flour. Soy flour is the starting material for production of soy concentrate and soy protein isolate. Defatted soy flour is obtained from solvent extracted flakes, and contains less than 1% oil. Full-fat soy flour is made from unextracted, dehulled beans, and contains about 18% to 20% oil. Due to its high oil content, a specialized Alpine Fine Impact Mill must be used for grinding rather than the more common hammer mill. Low-fat soy flour is made by adding back some oil to defatted soy flour. The lipid content varies according to specifications, usually between 4.5% and 9%. High-fat soy flour can also be produced by adding back soybean oil to defatted flour at the level of 15%. Lecithinated soy flour is made by adding soybean lecithin to defatted, low-fat or high-fat soy flours to increase their dispersibility and impart emulsifying properties. The lecithin content varies up to 15%.

For human consumption, soybean cultivar 3317361 can be used to produce edible protein ingredients which offer a healthier, less expensive replacement for animal protein in meats, as well as in dairy-type products. The soybeans produced by soybean cultivar 3317361 can be processed to produce a texture and appearance similar to many other foods. For example, soybeans are the primary ingredient in many dairy product substitutes (e.g., soy milk, margarine, soy ice cream, soy yogurt, soy cheese, and soy cream cheese) and meat substitutes (e.g., veggie burgers). These substitutes are readily available in most supermarkets. Although soy milk does not naturally contain significant amounts of digestible calcium (the high calcium content of soybeans is bound to the insoluble constituents and remains in the soy pulp), many manufacturers of soy milk sell calcium-enriched products as well. Soy is also used in tempeh: the beans (sometimes mixed with grain) are fermented into a solid cake.

Additionally, soybean cultivar 3317361 can be used to produce various types of "fillers" in meat and poultry products. Food service, retail, and institutional (primarily school lunch and correctional) facilities regularly use such "extended" products; that is, products which contain soy fillers. Extension may result in diminished flavor, but fat and cholesterol are reduced by adding soy fillers to certain products. Vitamin and mineral fortification can be used to make soy products nutritionally equivalent to animal protein; the protein quality is already roughly equivalent.

Tables

Table 2 shows the results obtained from a yield trial conducted over four locations (DeWitt, Ark.; Osceola, Ark.; Waldenburg, Ark.; and Cleveland, Miss.) in 2005. The planting dates were May 7, May 20, June 15, and April 19, respectively. The harvest dates were October 18, October 29, November 2, and September 18, respectively. All yield was calculated as bushels per acre. Column 1 shows the variety name, column 2 shows the mean yield from DeWitt, column 3 shows the mean yield from Osceola, column 4 shows the mean yield from Waldenburg, column 5 shows the mean yield from Cleveland, column 6 shows the mean yield of all four locations (columns 2-5), column 7 shows the average mean yield from the heavy clay soil location (Osceola), and column 8 shows the average mean yield from the light soil locations (DeWitt, Waldenburg, and Cleveland).

TABLE 2

| VARIETY | DW | OA | WG | CD | MEAN OF 4 LOC | CLAY SOILS | LIGHT SOILS |
|---|---|---|---|---|---|---|---|
| 3317361 | 81.9 | 66.8 | 51.0 | 64.8 | 66.1 | 66.8 | 65.9 |
| CS R5722N | 77.3 | 53.9 | 52.9 | 88.1 | 68.0 | 53.9 | 72.8 |
| HBK R5825 | 83.4 | 63.4 | 51.4 | 73.3 | 67.9 | 63.4 | 69.4 |
| S032552 | 83.3 | 60.7 | 40.1 | 66.0 | 62.5 | 60.7 | 63.1 |
| AG 5605 | 79.3 | 54.6 | 44.1 | 70.5 | 62.1 | 54.6 | 64.6 |
| P 95M80RR | 75.4 | 54.7 | 43.3 | 67.7 | 60.2 | 54.7 | 62.1 |
| S032359 | 63.8 | 60.6 | 44.9 | 68.2 | 59.4 | 60.6 | 59.0 |
| S032426 | 79.2 | 49.6 | 40.6 | 59.0 | 57.1 | 49.6 | 59.6 |
| S032351 | 64.6 | 54.3 | 45.3 | 62.2 | 56.6 | 54.3 | 57.4 |
| S032423 | 67.9 | 56.7 | 34.1 | 67.6 | 56.6 | 56.7 | 56.5 |
| S032437 | 60.0 | 52.2 | 36.1 | 77.4 | 56.4 | 52.2 | 57.8 |
| S032347 | 66.0 | 52.6 | 45.7 | 57.6 | 55.5 | 52.6 | 56.4 |
| S032414 | 69.7 | 54.2 | 43.1 | 54.4 | 55.3 | 54.2 | 55.7 |
| S032502 | 68.3 | 46.5 | 45.5 | 56.9 | 54.3 | 46.5 | 56.9 |
| S032503 | 61.1 | 52.0 | 43.1 | 50.7 | 51.7 | 52.0 | 51.6 |
| CV | 7.9 | 8.5 | 10.7 | 10.4 | 12 | | |
| Grand Mean | 72.1 | 55.5 | 44.1 | 65.6 | 59.3 | | |
| Heritability | 0.6 | 0.4 | 0.4 | 0.6 | 0.4 | | |
| LSD | 10 | 8.4 | 8.3 | 12 | 5.9 | | |
| R-Square | 0.8 | 0.7 | 0.7 | 0.8 | 0.8 | | |

Table 3 shows the results obtained from a trial conducted over two locations (DeWitt, Ark. and Osceola, Ark.) in 2005. The planting dates were May 7 and May 20, respectively. The harvest dates were October 18 and October 29, respectively. All yield was calculated as bushels per acre. Column 1 shows the variety name, column 2 shows the pubescence/pod color from DeWitt (where pubescence is characterized as G=Gray, T=Tawny (Brown), or LT=Light Tawny, and where pod color is characterized as T=Tan or B=Brown), column 3 shows the plant habit taken from DeWitt, column 4 shows the overall relative maturity, column 5 shows the overall average plant height in inches, column 6 shows the overall average lodging score, column 7 shows the Frogeye leaf spot rating from Osceola on a scale of 1-9 (where 1=having no spots and 9=being very heavy), column 8 shows the overall Sudden Death Syndrome infection rating on a scale of 1-9 (where 1=having no mottling and 9=being dead), column 9 shows the virus score from Osceola on a scale of 1-9 (where 1=having no virus and 9=having all plants affected), column 10 shows the bacterial pustule score from Osceola on a scale of 1-9 (where 1=having no pustules and 9=all leaves and plants affected), and column 11 shows the overall appearance score from Osceola on a scale of 1-9 (where 9=being adapted to the area, standing well, very uniform, and pretty to look at, and 1=being very ugly, having an unattractive lodging, and being ragged in appearance).

TABLE 3

| VARIETY | DW PUB/POD | DW H | RM | AVG PH | AVG LDG | OA FELS | AVG SDS | OA VIRUS | OA BP | OA APP |
|---|---|---|---|---|---|---|---|---|---|---|
| 3317361 | T/T | DET | 5.7 | 30 | 2.0 | 1.0 | 1.0 | 1.0 | 1.0 | 9.5 |
| CS R5722N | G/T | DET | 5.7 | 30 | 1.8 | 1.0 | 1.0 | 1.0 | 1.0 | 9.0 |
| HBK R5825 | T/T | DET | 5.8 | 33 | 1.8 | 1.0 | 1.0 | 1.0 | 1.0 | 9.5 |
| S032552 | G/T | DET | 5.7 | 31 | 2.2 | 2.0 | 1.0 | 1.0 | 1.0 | 8.5 |
| AG 5605 | G/B | DET | 5.6 | 28 | 1.5 | 2.0 | 2.0 | 1.0 | 1.0 | 8.5 |
| P 95M80RR | G/T | DET | 5.8 | 30 | 2.2 | 2.0 | 1.0 | 1.0 | 1.0 | 8.5 |
| S032359 | T/T | DET | 5.5 | 20 | 1.0 | 2.0 | 1.5 | 1.0 | 1.0 | 8.5 |
| S032426 | G/T | IND | 5.4 | 48 | 2.7 | 1.0 | 1.0 | 1.0 | 1.0 | 8.5 |
| S032351 | T/T | DET | 5.3 | 25 | 1.7 | 1.0 | 1.5 | 1.0 | 1.0 | 9.0 |
| S032423 | LT/B | IND | 5.7 | 42 | 2.2 | 1.0 | 1.5 | 1.0 | 1.0 | 9.0 |
| S032437 | T/T | DET | 5.7 | 24 | 2.0 | 2.0 | 1.0 | 1.0 | 1.0 | 8.5 |
| S032347 | T/B | DET | 5.3 | 26 | 1.8 | 2.0 | 1.5 | 1.0 | 1.0 | 9.0 |
| S032414 | T/T | DET | 5.6 | 25 | 2.2 | 2.5 | 1.5 | 1.0 | 1.0 | 8.5 |
| S032502 | T/T | DET | 5.6 | 25 | 1.7 | 1.0 | 1.0 | 1.0 | 1.0 | 9.0 |
| S032503 | T/T | DET | 5.6 | 28 | 1.7 | 1.0 | 1.0 | 1.0 | 1.0 | 9.0 |

Table 4 shows the results obtained from a trial conducted over four locations (Bonita, La.; Cleveland, Miss.; DeWitt, Ark.; and Waldenburg, Ark.) in 2006. The planting dates were May 15, May 21, May 22, and June 8, respectively. All yield was calculated as bushels per acre. Column 1 shows the variety name, column 2 shows the mean yield from Bonita, column 3 shows the mean yield from Cleveland, column 4 shows the mean yield from DeWitt, column 5 shows the mean yield from Waldenburg, column 6 shows the mean yield of all four locations (columns 2-5), column 7 shows the mean yield of the variety as a percentage of the grand mean yield, and column 8 shows the mean yield as a percentage of the check mean yield.

Table 5 shows the results obtained from a trial conducted over four locations (DeWitt, Ark.; Bonita, La.; Cleveland, Miss.; and Waldenburg, Ark.) in 2006 for various agronomic characteristics. Column 1 shows the variety name, column 2 shows the maturity date from DeWitt, column 3 shows the pubescence/pod color from DeWitt (where pubescence is characterized as G=Gray, T=Tawny (Brown), or LT=Light Tawny, and where pod color is characterized as T=Tan or B=Brown), column 4 shows the plant habit from DeWitt, column 5 shows the average plant height in inches from Bonita, Dewitt, and Waldenburg, column 6 shows the average lodging score from Bonita, Dewitt, and Waldenburg, column 7 shows the overall appearance score from DeWitt on a scale

TABLE 4

| VARIETY | BA | CD | DW | WG | MEAN OF 4 LOC | % OF GRAND MEAN | % OF CHECK MEAN |
|---|---|---|---|---|---|---|---|
| 3317361 | 54.1 | 68.6 | 95.7 | 58.0 | 69.1 | 105.7 | 105.7 |
| OZARK | 62.7 | 80.3 | 76.7 | 60.8 | 70.1 | 107.3 | 107.2 |
| HBK 5991 | 59.3 | 70.9 | 81.6 | 63.2 | 68.7 | 105.2 | 105.1 |
| S032483 | 53.5 | 83.5 | 75.2 | 58.4 | 67.6 | 103.5 | 103.4 |
| R97-1634 | 64.6 | 67.8 | 78.6 | 59.2 | 67.5 | 103.3 | 103.3 |
| S032486 | 51.2 | 74.8 | 83.5 | 60.3 | 67.4 | 103.2 | 103.1 |
| S000875 | 54.7 | 71.4 | 76.1 | 64.4 | 66.6 | 102.0 | 101.9 |
| DP 5989 | 56.6 | 64.9 | 84.5 | 59.4 | 66.3 | 101.5 | 101.5 |
| S022010 | 51.1 | 75.2 | 90.6 | 47.8 | 66.1 | 101.2 | 101.2 |
| TN 5601T | 54.5 | 70.3 | 87.1 | 48.4 | 65.1 | 99.6 | 99.5 |
| HUTCHESON | 48.1 | 66.1 | 86.7 | 58.4 | 64.8 | 99.2 | 99.1 |
| S032484 | 57.4 | 66.7 | 70.1 | 64.1 | 64.6 | 98.8 | 98.7 |
| HBK R5825 | 52.5 | 74.8 | 82.0 | 48.5 | 64.4 | 98.6 | 98.6 |
| HBK C5894 | 56.9 | 67.6 | 74.8 | 57.2 | 64.1 | 98.1 | 98.1 |
| S022012 | 48.4 | 75.2 | 80.5 | 52.1 | 64.0 | 98.0 | 97.9 |
| S011243 | 61.0 | 61.6 | 77.4 | 52.7 | 63.2 | 96.7 | 96.6 |
| S032552 | 47.1 | 66.2 | 83.0 | 53.0 | 62.3 | 95.4 | 95.3 |
| S011241 | 51.2 | 62.7 | 75.2 | 59.4 | 62.1 | 95.1 | 95.0 |
| AG 5905 | 42.5 | 66.1 | 85.5 | 52.4 | 61.6 | 94.3 | 94.2 |
| HBK R5924 | 52.8 | 68.5 | 71.2 | 52.0 | 61.1 | 93.5 | 93.4 |
| Check Mean | 55 | 69.7 | 80.8 | 55.9 | 65.4 | | |
| CV | 8.1 | 6.8 | 9.3 | 6.4 | 10.4 | | |
| Grand Mean | 54 | 70.1 | 80.8 | 56.5 | 65.3 | | |
| Heritability | 0.5 | 0.5 | 0.2 | 0.6 | 0 | | |
| LSD | 7.6 | 8.2 | 13 | 6.2 | 5.6 | | |
| R-Square | 0.8 | 0.7 | 0.6 | 0.8 | 0.8 | | |
| Residual | 19.2 | 22.6 | 56.2 | 13 | 46.1 | | |
| SED | 4.4 | 4.8 | 7.5 | 3.6 | 3.4 | | | of 1-9 (where 9=being adapted to the area, standing well, very uniform, and pretty to look at, and 1=being very ugly, having an unattractive lodging, and being ragged in appearance), and column 8 shows the overall Sudden Death Syndrome infection rating from Cleveland on a scale of 1-9 (where 1=having no mottling and 9=being dead).

TABLE 5

| VARIETY | DW MD | DW PUB/ POD | DW H | AVG PH | AVG LDG | DW APP | CD SDS |
|---|---|---|---|---|---|---|---|
| 3317361 | 10/2 | T/T | DET | 35 | 1.7 | 7.0 | 3.0 |
| OZARK | 9/28 | G/T | DET | 29 | 1.7 | 6.0 | 7.0 |
| HBK 5991 | 10/2 | T/T | DET | 32 | 2.3 | 4.0 | 4.0 |
| S032483 | 10/2 | T/T | DET | 30 | 1.8 | 7.0 | 4.0 |
| R97-1634 | 10/3 | G/T | DET | 30 | 1.7 | 7.0 | 5.0 |
| S032486 | 10/3 | T/T | DET | 32 | 1.5 | 7.0 | 2.0 |
| S000875 | 10/4 | G/T | DET | 32 | 1.8 | 7.0 | 3.0 |
| DP 5989 | 10/3 | T/T | DET | 47 | 2.9 | 4.0 | 7.0 |
| S022010 | 10/3 | T/T | DET | 33 | 1.6 | 7.0 | 1.0 |
| TN 5601T | 10/1 | G/T | DET | 32 | 1.8 | 7.0 | 7.0 |
| HUTCHESON | 10/1 | G/T | DET | 31 | 1.8 | 5.0 | 5.0 |
| S032484 | 10/4 | T/T | DET | 30 | 2.0 | 4.0 | 5.0 |
| HBK R5825 | 10/3 | T/T | DET | 31 | 1.8 | 5.0 | 2.0 |
| HBK C5894 | 10/4 | G/T | DET | 36 | 2.4 | 4.0 | 3.0 |
| S022012 | 10/2 | T/T | DET | 32 | 1.7 | 7.0 | 5.0 |
| S011243 | 10/3 | LT/B | IND | 39 | 1.7 | 6.0 | 6.0 |
| S032552 | 10/5 | G/T | DET | 40 | 2.2 | 6.0 | 5.0 |
| S011241 | 10/4 | LT/B | IND | 45 | 2.1 | 5.0 | 5.0 |
| AG 5905 | 10/2 | G/T | DET | 36 | 1.7 | 7.0 | 5.0 |
| HBK R5924 | 10/4 | G/T | DET | 38 | 2.8 | 5.0 | 6.0 |

Table 6 shows the results obtained from a trial conducted over three locations (DeWitt, Ark.; Cleveland, Miss.; and Waldenburg, Ark.) in 2007. The planting dates were May 22, May 19, and May 22, respectively. The harvest dates were November 11, November 2, and November 14, respectively. All yield was calculated as bushels per acre. Column 1 shows the variety name, column 2 shows the mean yield from DeWitt, column 3 shows the mean yield from Cleveland, column 4 shows the mean yield from Waldenburg, column 5 shows the mean yield of all three locations (columns 2-4), column 6 shows the mean yield of the variety as a percentage of the grand mean yield, and column 7 shows the mean yield as a percentage of the check mean yield.

TABLE 6

| VARIETY | DW | CD | WG | MEAN OF 3 LOC | % OF GRAND MEAN | % OF CHECK MEAN |
|---|---|---|---|---|---|---|
| 3317361 | 89.0 | 51.5 | 45.1 | 61.9 | 110.1 | 108.0 |
| S043783C | 87.6 | 62.2 | 47.4 | 65.7 | 117.0 | 114.7 |
| S001185 | 87.0 | 62.5 | 45.1 | 64.9 | 115.4 | 113.2 |
| HBK 5991 | 77.4 | 69.6 | 46.3 | 64.4 | 114.6 | 112.3 |
| S044076C | 74.4 | 63.9 | 47.8 | 62.0 | 110.4 | 108.2 |
| S043791C | 88.7 | 49.9 | 46.7 | 61.8 | 109.9 | 107.8 |
| HBK C5894 | 77.9 | 60.0 | 44.2 | 60.7 | 108.0 | 105.9 |
| S022010 | 76.4 | 64.1 | 41.1 | 60.5 | 107.7 | 105.6 |
| S011243 | 75.7 | 59.6 | 43.1 | 59.4 | 105.8 | 103.7 |
| S000875 | 74.1 | 58.2 | 44.7 | 59.0 | 105.0 | 102.9 |
| S043496C | 69.8 | 55.5 | 50.9 | 58.7 | 104.5 | 102.4 |
| S043702C | 67.4 | 62.3 | 44.8 | 58.2 | 103.5 | 101.5 |
| AG 5905 | 74.9 | 49.7 | 48.6 | 57.7 | 102.7 | 100.7 |
| S011241 | 72.9 | 55.0 | 44.3 | 57.4 | 102.1 | 100.1 |
| R98-1821 | 69.3 | 63.0 | 39.8 | 57.3 | 102.1 | 100.1 |
| S001189 | 71.3 | 56.2 | 43.7 | 57.0 | 101.5 | 99.5 |
| DP 5989 | 80.4 | 47.7 | 41.9 | 56.6 | 100.7 | 98.8 |
| S043792C | 76.6 | 47.0 | 46.1 | 56.5 | 100.6 | 98.7 |
| OZARK | 64.9 | 59.5 | 44.7 | 56.3 | 100.3 | 98.3 |
| S044063C | 69.8 | 52.4 | 43.0 | 55.1 | 98.0 | 96.1 |
| HUTCHESON | 65.6 | 57.0 | 39.0 | 53.9 | 95.9 | 94.0 |
| S043670CFB | 73.2 | 43.4 | 40.4 | 52.3 | 93.1 | 91.3 |

TABLE 6-continued

| VARIETY | DW | CD | WG | MEAN OF 3 LOC | % OF GRAND MEAN | % OF CHECK MEAN |
|---|---|---|---|---|---|---|
| S043431C | 62.6 | 53.1 | 39.3 | 51.7 | 91.9 | 90.1 |
| TN 5601T | 65.3 | 43.2 | 46.4 | 51.6 | 91.9 | 90.1 |
| S044043C | 67.8 | 44.7 | 42.1 | 51.5 | 91.7 | 89.9 |
| S043943C | 68.6 | 43.7 | 36.9 | 49.7 | 88.4 | 86.7 |
| S044064C | 66.9 | 48.2 | 34.0 | 49.7 | 88.5 | 86.7 |
| S044122FB | 71.9 | 34.5 | 33.8 | 46.7 | 83.2 | 81.5 |
| S044147FB | 57.2 | 40.7 | 39.3 | 45.7 | 81.4 | 79.8 |
| S043667CFB | 57.7 | 36.6 | 31.0 | 41.7 | 74.3 | 72.8 |
| Check Mean | 72.3 | 55.2 | 44.4 | 57.3 | 0 | 0 |
| CV | 11 | 9.6 | 11.4 | 10.9 | 0 | 0 |
| Grand Mean | 72.7 | 53.1 | 42.7 | 56.2 | 0 | 0 |
| Heritability | 0.4 | 0.7 | 0.3 | 0.7 | 0 | 0 |
| LSD | 13.7 | 8.6 | 8.3 | 5.9 | 0 | 0 |
| R-Square | 0.7 | 0.9 | 0.7 | 0.9 | 0 | 0 |
| Residual | 64.4 | 25.8 | 23.6 | 37.3 | 0 | 0 |
| SED | 8 | 5.1 | 4.9 | 3.5 | 0 | 0 |

Table 7 shows the results obtained from a trial conducted over three locations (DeWitt, Ark.; Cleveland, Miss.; and Waldenburg, Ark.) in 2007 for various agronomic characteristics. Column 1 shows the variety name, column 2 shows the plant habit from DeWitt, column 3 shows the maturity date from DeWitt, column 4 shows the pubescence/pod color from DeWitt (where pubescence is characterized as G=Gray, T=Tawny (Brown), or LT=Light Tawny, and where pod color is characterized as T=Tan or B=Brown), column 5 shows the average plant height in inches from Dewitt, Cleveland, and Waldenburg, column 6 shows the average lodging score from Dewitt, Cleveland, and Waldenburg, column 7 shows the overall appearance score from Dewitt, Cleveland, and Waldenburg on a scale of 1-9 (where 9=being adapted to the area, standing well, very uniform, and pretty to look at, and 1=being very ugly, having an unattractive lodging, and being ragged in appearance), column 8 shows the Frogeye leaf spot rating from Cleveland on a scale of 1-9 (where 1=having no spots and 9=being very heavy), and column 9 shows the overall Sudden Death Syndrome infection rating from Cleveland on a scale of 1-9 (where 1=having no mottling and 9=being dead).

TABLE 7

| VARIETY | DW H | DW MD | DW PUB/ POD | AVG PH | AVG LDG | AVG APP | CD FELS | CD SDS |
|---|---|---|---|---|---|---|---|---|
| 3317361 | DET | 10/1 | T/T | 38 | 1.7 | 8.0 | 1.0 | 2.0 |
| S043783C | DET | 10/5 | G/T | 36 | 1.1 | 9.0 | 0.0 | 1.0 |
| S001185 | DET | 10/1 | T/T | 38 | 1.7 | 8.0 | 0.0 | 0.0 |
| HBK 5991 | DET | 9/30 | G/T | 35 | 1.8 | 7.0 | 0.0 | 0.0 |
| S044076C | DET | 10/1 | T/T | 30 | 1.0 | 7.0 | 0.0 | 0.0 |
| S043791C | DET | 9/1 | G/T | 30 | 1.3 | 7.5 | 0.0 | 0.0 |
| HBK C5894 | DET | 9/30 | G/T | 39 | 2.8 | 6.5 | 0.0 | 0.0 |
| S022010 | DET | 10/2 | T/T | 38 | 1.3 | 8.5 | 1.0 | 0.0 |
| S011243 | DET | 9/30 | T/T | 45 | 2.2 | 8.0 | 0.0 | 2.0 |
| S000875 | DET | 9/30 | G/T | 34 | 2.1 | 6.5 | 0.0 | 0.0 |
| S043496C | DET | 9/29 | T/T | 35 | 1.5 | 7.5 | 0.0 | 0.0 |
| S043702C | DET | 10/5 | T/T | 38 | 1.7 | 8.5 | 1.0 | 0.0 |
| AG 5905 | DET | 10/1 | G/T | 41 | 1.8 | 7.5 | 0.0 | 2.0 |
| S011241 | IND | 10/2 | LT/B | 54 | 2.8 | 7.0 | 0.0 | 3.0 |
| R98-1821 | DET | 9/29 | T/T | 33 | 1.0 | 8.5 | 0.0 | 0.0 |
| S001189 | DET | 10/2 | G/T | 35 | 1.8 | 7.0 | 0.0 | 2.0 |
| DP 5989 |  |  |  | 51 | 2.3 | 7.0 | 0.0 | 0.0 |
| S043792C | IND | 9/30 | G/B | 37 | 1.7 | 7.5 | 1.0 | 4.0 |
| OZARK | DET | 9/30 | G/T | 35 | 1.8 | 7.5 | 1.0 | 2.0 |
| S044063C | IND | 9/29 | G/T | 53 | 2.3 | 7.0 | 0.0 | 0.0 |
| HUTCHESON | DET | 10/1 | G/T | 34 | 1.5 | 7.5 | 1.0 | 2.0 |
| S043670CFB | DET | 10/9 | G/T | 38 | 1.9 | 8.0 | 1.0 | 0.0 |
| S043431C | DET | 10/1 | T/T | 35 | 1.5 | 7.5 | 0.0 | 0.0 |

TABLE 7-continued

| VARIETY | DW H | DW MD | DW PUB/ POD | AVG PH | AVG LDG | AVG APP | CD FELS | CD SDS |
|---|---|---|---|---|---|---|---|---|
| TN 5601T | DET | 10/3 | G/T | 36 | 1.6 | 7.5 | 1.0 | 1.0 |
| S044043C | DET | 9/29 | T/T | 41 | 2.6 | 5.5 | 2.0 | 1.0 |
| S043943C | IND | 9/29 | G/T | 56 | 2.9 | 5.5 | 0.0 | 1.0 |
| S044064C | IND | 9/30 | T/T | 57 | 2.5 | 6.5 | 0.0 | 0.0 |
| S044122FB | DET | 10/6 | G/T | 36 | 1.8 | 6.5 | 0.0 | 0.0 |
| S044147FB | DET | 10/1 | LT/B | 38 | 1.7 | 7.5 | 1.0 | 3.0 |
| S043667CFB | DET | 10/1 | G/T | 36 | 1.9 | 7.0 | 0.0 | 0.0 |

Table 8 shows the results obtained from a trial conducted over seven locations (Cleveland, Miss.; Keiser, Ark.; Morganza, La.; McGehee, Ark.; Matthews, Mo.; Union City, Tenn.; and Weiner, Ark.) in 2009. The planting dates were May 30, June 2, May 11, April 29, July 8, June 30, and June 20, respectively. The harvest dates were November 5, November 14, October 19, November 10, December 1, November 28, and November 19, respectively. All yield was calculated as bushels per acre. Column 1 shows the variety name, column 2 shows the mean yield from Cleveland, column 3 shows the mean yield from Keiser, column 4 shows the mean yield from Morganza, column 5 shows the mean yield from McGehee, column 6 shows the mean yield from Matthews, column 7 shows the mean yield from Union City, column 8 shows the mean yield from Weiner, column 9 shows the mean yield of all seven locations (columns 2-8), column 10 shows the mean yield of the variety as a percentage of the grand mean yield, and column 11 shows the mean yield as a percentage of the check mean yield.

TABLE 8

| VARIETY | CD | KR | MA | ME | MS | UC | WR | MEAN OF 7 LOC | % OF GRAND MEAN | % OF CHECK MEAN |
|---|---|---|---|---|---|---|---|---|---|---|
| 3317361 | 49.8 | 58.4 | 44.3 | 53.2 | 41.9 | 47.2 | 36.5 | 47.3 | 105.3 | 102.8 |
| S001185 | 51.2 | 66.2 | 54.2 | 61.5 | 46.3 | 45.9 | 36.8 | 51.7 | 115.1 | 112.4 |
| TN 5601T | 53.8 | 70.0 | 49.8 | 40.9 | 48.2 | 51.6 | 47.8 | 51.7 | 115.1 | 112.4 |
| S044076C | 52.1 | 65.4 | 51.7 | 58.5 | 43.3 | 47.3 | 36.2 | 50.6 | 112.7 | 110.0 |
| R03-1250 | 57.4 | 67.5 | 51.9 | 44.4 | 43.8 | 55.6 | 33.0 | 50.5 | 112.4 | 109.8 |
| S001177 | 54.8 | 58.1 | 58.9 | 57.4 | 41.7 | 53.0 | 25.8 | 49.9 | 111.2 | 108.6 |
| S022010 | 52.7 | 60.5 | 49.8 | 43.8 | 48.2 | 52.1 | 37.6 | 49.2 | 109.6 | 107.0 |
| R01-3474F | 48.4 | 55.8 | 51.7 | 41.3 | 47.8 | 52.5 | 46.3 | 49.1 | 109.3 | 106.7 |
| S044063C | 51.8 | 58.0 | 49.6 | 51.0 | 44.2 | 54.2 | 34.5 | 49.0 | 109.2 | 106.6 |
| S022460 | 49.7 | 69.8 | 47.6 | 41.2 | 47.9 | 50.9 | 34.7 | 48.8 | 108.6 | 106.1 |
| HBK C5894 | 53.2 | 65.1 | 48.3 | 38.9 | 63.1 | 42.5 | 28.6 | 48.5 | 108.0 | 105.4 |
| S011241 | 56.2 | 56.8 | 41.6 | 52.6 | 49.6 | 50.0 | 32.7 | 48.5 | 107.9 | 105.4 |
| AG 5503 | 64.0 | 66.3 | 52.3 | 32.2 | 38.7 | 55.2 | 29.7 | 48.3 | 107.6 | 105.0 |
| JAKE | 59.6 | 61.2 | 47.6 | 26.6 | 52.1 | 54.9 | 36.1 | 48.3 | 107.5 | 105.0 |
| S000875 | 52.7 | 59.6 | 50.2 | 45.0 | 41.6 | 50.1 | 36.1 | 47.9 | 106.6 | 104.1 |
| OZARK | 53.7 | 63.7 | 54.4 | 30.3 | 46.2 | 54.1 | 32.4 | 47.8 | 106.5 | 103.9 |
| S043791C | 44.3 | 59.3 | 46.1 | 41.5 | 48.4 | 56.9 | 33.3 | 47.1 | 104.9 | 102.4 |
| S043702C | 48.8 | 52.4 | 54.3 | 49.9 | 47.8 | 46.6 | 29.5 | 47.0 | 104.6 | 102.2 |
| R03-1011 | 48.5 | 51.8 | 48.5 | 53.5 | 42.3 | 49.0 | 32.1 | 46.5 | 103.6 | 101.1 |
| CS RX667 | 43.9 | 53.7 | 43.2 | 53.9 | 41.8 | 50.7 | 38.7 | 46.5 | 103.6 | 101.2 |
| R02-3065 | 54.1 | 63.5 | 43.0 | 38.9 | 44.0 | 47.1 | 34.2 | 46.4 | 103.3 | 100.8 |
| S043785C | 42.3 | 55.6 | 45.7 | 52.3 | 39.5 | 49.8 | 37.8 | 46.1 | 102.7 | 100.3 |
| S022395 | 50.2 | 59.8 | 47.4 | 43.5 | 40.7 | 46.3 | 34.1 | 46.0 | 102.4 | 99.9 |
| DILLON | 39.6 | 55.2 | 48.7 | 49.1 | 37.6 | 50.3 | 35.6 | 45.1 | 100.5 | 98.1 |
| S001189 | 48.4 | 55.5 | 34.0 | 43.5 | 48.4 | 44.6 | 27.5 | 43.1 | 95.9 | 93.7 |
| NC ROY | 31.8 | 49.1 | 43.7 | 52.0 | 43.8 | 45.4 | 36.2 | 43.1 | 96.0 | 93.7 |
| TN 5002T | 55.2 | 55.4 | 46.7 | 22.8 | 40.2 | 48.2 | 32.0 | 42.9 | 95.5 | 93.2 |
| RM1091FB | 47.1 | 45.1 | 45.5 | 43.3 | 38.2 | 43.0 | 37.9 | 42.8 | 95.4 | 93.1 |
| RM20673FB | 38.7 | 52.8 | 34.6 | 53.2 | 40.5 | 41.2 | 36.5 | 42.5 | 94.6 | 92.3 |
| RM7269FB | 38.8 | 55.6 | 42.4 | 44.3 | 34.6 | 43.4 | 37.7 | 42.4 | 94.4 | 92.1 |
| RM22555FB | 45.4 | 49.9 | 35.0 | 48.3 | 34.2 | 46.6 | 30.8 | 41.4 | 92.2 | 90.1 |
| RM22347FB | 41.3 | 51.8 | 40.6 | 36.8 | 36.0 | 39.5 | 37.3 | 40.5 | 90.1 | 87.9 |
| RM1144FB | 45.5 | 49.7 | 36.8 | 39.5 | 35.6 | 39.9 | 26.0 | 39.0 | 86.8 | 84.7 |
| RM10109FB | 35.2 | 55.4 | 30.5 | 47.4 | 38.6 | 34.4 | 28.0 | 38.5 | 85.7 | 83.6 |
| RM7532FB | 38.4 | 46.6 | 35.2 | 41.9 | 36.3 | 40.5 | 30.4 | 38.4 | 85.6 | 83.6 |
| RM7492FB | 38.7 | 45.9 | 37.3 | 43.6 | 35.9 | 37.7 | 29.2 | 38.3 | 85.3 | 83.3 |
| RM6084FB | 36.8 | 45.8 | 38.8 | 42.0 | 37.2 | 36.8 | 26.8 | 37.7 | 84.0 | 82.0 |
| S043792C | 55.2 | 57.6 | 52.9 | 1.0 | 28.9 | 21.8 | 37.3 | 37.9 | 82.9 | 81.0 |
| RM20380FB | 35.9 | 32.2 | 28.3 | 43.8 | 40.4 | 40.4 | 28.5 | 35.6 | 79.3 | 77.4 |
| HUTCHESON | 29.7 | 43.3 | 42.1 | 35.6 | 34.2 | 37.9 | 24.6 | 35.3 | 78.6 | 76.8 |
| Check Mean | 49.1 | 58.1 | 47.1 | 39.5 | 45.0 | 49.1 | 34.0 | 46.0 | | |
| CV | 6.8 | 8.8 | 12.3 | 15.8 | 11.6 | 9.0 | 17.0 | 15.9 | | |
| Grand Mean | 47.3 | 56.1 | 45.1 | 44.5 | 41.5 | 46.5 | 33.3 | 44.9 | | |
| Heritability | 0.9 | 0.7 | 0.5 | 0.5 | 0.7 | 0.7 | 0.3 | 0.4 | | |
| LSD | 5.4 | 8.4 | 9.4 | 11.8 | 8.1 | 7.1 | 9.5 | 4.5 | | |
| R-Square | 0.9 | 0.8 | 0.8 | 0.7 | 0.9 | 0.8 | 0.6 | 0.6 | | |
| Residual | 10.3 | 24.6 | 31.0 | 49.4 | 23.2 | 17.6 | 32.0 | 51.2 | | |
| SED | 3.2 | 5.0 | 5.6 | 7.0 | 4.8 | 4.2 | 5.7 | 7.2 | | |

Table 9 shows the results obtained from a trial conducted over seven locations (Cleveland, Miss.; Keiser, Ark.; Morganza, La.; McGehee, Ark.; Matthews, Mo.; Union City, Tenn.; and Weiner, Ark.) in 2009 for various agronomic characteristics. Column 1 shows the variety name, column 2 shows the average plant height in inches from Cleveland, column 3 shows the average plant height in inches from Morganza, column 4 shows the shows the average plant height in inches from Cleveland and Morganza, column 5 shows the average lodging score from Cleveland, column 7 shows the average lodging score from Moganza, and column 8 shows the average lodging score from Cleveland and Moganza.

TABLE 9

| VARIETY | CD PH | MA PH | AVG PH | CD LDG | MA LDG | AVG LDG |
|---|---|---|---|---|---|---|
| 3317361 | 39 | 38 | 39 | 2.0 | 1.0 | 1.5 |
| S001185 | 36 | 37 | 37 | 2.0 | 3.0 | 2.5 |
| TN 5601T | 41 | 37 | 39 | 3.0 | 2.0 | 2.5 |
| S044076C | 37 | 29 | 33 | 2.0 | 1.0 | 1.5 |
| R03-1250 | 39 | 32 | 36 | 1.0 | 1.0 | 1.0 |
| S001177 | 39 | 41 | 40 | 2.0 | 1.0 | 1.5 |
| S022010 | 39 | 36 | 38 | 2.0 | 1.0 | 1.5 |
| R01-3474F | 42 | 34 | 38 | 3.0 | 2.0 | 2.5 |
| S044063C | 49 | 48 | 49 | 2.0 | 3.0 | 2.5 |
| S022460 | 41 | 39 | 40 | 2.0 | 1.0 | 1.5 |
| HBK C5894 | 47 | 41 | 44 | 3.0 | 3.0 | 3.0 |
| S011241 | 48 | 49 | 49 | 3.0 | 3.0 | 3.0 |
| AG 5503 | 46 | 47 | 47 | 2.0 | 2.0 | 2.0 |
| JAKE | 37 | 29 | 33 | 2.0 | 1.0 | 1.5 |
| S000875 | 38 | 29 | 34 | 3.0 | 2.0 | 2.5 |
| OZARK | 34 | 31 | 33 | 2.0 | 1.0 | 1.5 |
| S043791C | 44 | 46 | 45 | 3.0 | 3.0 | 3.0 |
| S043702C | 38 | 35 | 37 | 1.0 | 1.0 | 1.0 |
| R03-1011 | 34 | 33 | 34 | 2.0 | 1.0 | 1.5 |
| CS RX667 | 47 | 41 | 44 | 3.0 | 2.0 | 2.5 |
| R02-3065 | 36 | 34 | 35 | 2.0 | 1.0 | 1.5 |
| S043785C | 40 | 34 | 37 | 2.0 | 1.0 | 1.5 |
| S022395 | 40 | 39 | 40 | 3.0 | 2.0 | 2.5 |
| DILLON | 38 | 35 | 37 | 3.0 | 2.0 | 2.5 |
| S001189 | 37 | 37 | 37 | 2.0 | 3.0 | 2.5 |
| NC ROY | 38 | 37 | 38 | 3.0 | 4.0 | 3.5 |
| TN 5002T | 38 | 28 | 33 | 2.0 | 1.0 | 1.5 |
| RM1091FB | 39 | 30 | 35 | 3.0 | 1.0 | 2.0 |
| RM20673FB | 39 | 34 | 37 | 3.0 | 2.0 | 2.5 |
| RM7269FB | 39 | 33 | 36 | 3.0 | 1.0 | 2.0 |
| RM22555FB | 38 | 28 | 33 | 3.0 | 1.0 | 2.0 |
| RM22347FB | 39 | 33 | 36 | 3.0 | 1.0 | 2.0 |
| RM1144FB | 40 | 26 | 33 | 3.0 | 1.0 | 2.0 |
| RM10109FB | 38 | 35 | 37 | 3.0 | 3.0 | 3.0 |
| RM7532FB | 40 | 36 | 38 | 3.0 | 2.0 | 2.5 |
| RM7492FB | 39 | 29 | 34 | 3.0 | 1.0 | 2.0 |
| RM6084FB | 38 | 36 | 37 | 3.0 | 2.0 | 2.5 |
| S043792C | 45 | 50 | 48 | 2.0 | 3.0 | 2.5 |
| RM20380FB | 38 | 39 | 39 | 3.0 | 2.0 | 2.5 |
| HUTCHESON | 38 | 30 | 34 | 4.0 | 2.0 | 3.0 |

Table 10 shows the results obtained from a trial conducted over six locations (Cleveland, Miss.; Clarksdale, Miss.; DeWitt, Ark.; Keiser, Ark.; Morganza, La.; and Weiner, Ark.) in 2008. The planting dates were May 14, May 21, May 21, June 6, April 18, and May 29, respectively. The harvest dates were November 7, November 5, October 20, November 1, October 9, and October 25, respectively. All yield was calculated as bushels per acre. Column 1 shows the variety name, column 2 shows the mean yield from Cleveland, column 3 shows the mean yield from Clarksdale, column 4 shows the mean yield from DeWitt, column 5 shows the mean yield from Keiser, column 6 shows the mean yield from Morganza, column 7 shows the mean yield from Weiner, column 8 shows the mean yield of all six locations (columns 2-7), column 9 shows the mean yield of the variety as a percentage of the grand mean yield, and column 10 shows the mean yield as a percentage of the check mean yield.

TABLE 10

| VARIETY | CD | CE | DW | KR | MA | WR | MEAN OF 6 LOC | % OF GRAND MEAN | % OF CHECK MEAN |
|---|---|---|---|---|---|---|---|---|---|
| 3317361 | 50.1 | 52.1 | 63.7 | 63.7 | 54.1 | 71.0 | 59.1 | 111.1 | 108.6 |
| S044076C | 43.3 | 75.5 | 75.6 | 61.3 | 53.3 | 68.9 | 63.0 | 118.4 | 115.7 |
| S000875 | 55.4 | 78.2 | 58.8 | 68.2 | 42.0 | 73.1 | 62.6 | 117.7 | 115.0 |
| S043702C | 59.8 | 79.3 | 50.5 | 67.9 | 47.8 | 67.3 | 62.1 | 116.7 | 114.1 |
| S022010 | 58.1 | 65.6 | 71.6 | 53.5 | 51.5 | 66.6 | 61.1 | 114.9 | 112.4 |
| R01-3474F | 52.6 | 70.7 | 62.3 | 71.4 | 40.6 | 68.3 | 61.0 | 114.6 | 112.0 |
| S001185 | 52.0 | 66.9 | 67.2 | 62.0 | 53.2 | 63.2 | 60.7 | 114.2 | 111.6 |
| S043791C | 42.4 | 75.4 | 58.1 | 61.7 | 57.1 | 67.2 | 60.3 | 113.3 | 110.8 |
| S011241 | 41.7 | 51.6 | 62.5 | 72.9 | 61.6 | 66.0 | 59.4 | 111.6 | 109.1 |
| S043785C | 45.7 | 65.5 | 73.0 | 69.5 | 37.4 | 63.7 | 59.1 | 111.1 | 108.6 |
| S001177 | 47.1 | 71.5 | 64.0 | 61.9 | 51.4 | 54.9 | 58.4 | 109.9 | 107.4 |
| NC ROY | 53.1 | 52.8 | 66.4 | 72.2 | 25.3 | 78.1 | 58.0 | 109.0 | 106.5 |
| S001189 | 48.8 | 62.9 | 61.2 | 56.9 | 45.1 | 72.2 | 57.8 | 108.7 | 106.3 |
| TN 5601T | 50.9 | 74.3 | 64.3 | 57.3 | 26.8 | 72.1 | 57.6 | 108.3 | 105.9 |
| S044063C | 49.9 | 59.2 | 71.3 | 53.4 | 43.3 | 66.8 | 57.3 | 107.7 | 105.3 |
| S022395 | 56.0 | 52.8 | 63.2 | 57.1 | 40.1 | 72.6 | 56.9 | 107.0 | 104.6 |
| S022460 | 44.0 | 63.3 | 66.5 | 52.3 | 47.8 | 66.4 | 56.7 | 106.6 | 104.2 |
| HBK 5991 | 40.1 | 61.9 | 66.7 | 52.6 | 52.2 | 66.7 | 56.7 | 106.6 | 104.2 |
| S022279 | 54.2 | 49.2 | 60.0 | 55.6 | 46.1 | 73.4 | 56.4 | 106.0 | 103.7 |
| S032596 | 41.4 | 57.8 | 60.9 | 57.1 | 50.7 | 67.2 | 55.8 | 104.9 | 102.6 |
| OZARK | 62.4 | 64.1 | 55.7 | 52.4 | 26.3 | 68.6 | 54.9 | 103.2 | 100.9 |
| S043783C | 52.2 | 59.5 | 54.8 | 41.6 | 50.3 | 70.3 | 54.8 | 103.0 | 100.6 |
| S022012 | 47.0 | 62.6 | 57.9 | 62.0 | 30.7 | 66.4 | 54.4 | 102.3 | 100.0 |
| S043756C | 54.2 | 63.6 | 55.3 | 56.7 | 23.5 | 68.8 | 53.7 | 100.9 | 98.6 |
| S044043C | 38.9 | 71.5 | 67.0 | 45.2 | 36.9 | 63.2 | 53.7 | 101.0 | 98.8 |
| S044064C | 41.3 | 63.7 | 72.4 | 49.8 | 35.6 | 48.7 | 51.9 | 97.6 | 95.4 |
| S022009 | 39.4 | 45.9 | 53.5 | 57.7 | 48.9 | 65.3 | 51.8 | 97.3 | 95.1 |
| S043792C | 40.7 | 55.7 | 49.1 | 43.5 | 42.3 | 68.7 | 50.0 | 94.0 | 91.8 |
| S043496C | 44.3 | 51.9 | 51.6 | 58.4 | 27.2 | 61.5 | 49.1 | 92.3 | 90.2 |

TABLE 10-continued

| VARIETY | CD | CE | DW | KR | MA | WR | MEAN OF 6 LOC | % OF GRAND MEAN | % OF CHECK MEAN |
|---|---|---|---|---|---|---|---|---|---|
| S043629CFB | 44.0 | 53.8 | 51.7 | 59.3 | 24.5 | 58.1 | 48.6 | 91.3 | 89.2 |
| S043627CFB | 44.9 | 49.7 | 60.3 | 55.5 | 10.7 | 63.6 | 47.4 | 89.2 | 87.1 |
| S044122FB | 44.4 | 48.3 | 54.6 | 45.3 | 24.7 | 67.2 | 47.4 | 89.1 | 87.1 |
| S043494C | 49.3 | 44.7 | 51.9 | 52.8 | 19.0 | 64.2 | 47.0 | 88.3 | 86.3 |
| S043943C | 31.8 | 46.0 | 65.7 | 41.4 | 31.7 | 52.7 | 44.9 | 84.3 | 82.4 |
| S044077C | 53.4 | 51.6 | 52.2 | 40.7 | 7.7 | 52.3 | 43.0 | 80.8 | 79.0 |
| S04-9344 | 39.2 | 67.7 | 37.5 | 35.9 | 20.5 | 50.8 | 41.9 | 78.8 | 77.1 |
| S043670CFB | 40.0 | 50.4 | 35.7 | 45.0 | 10.6 | 59.8 | 40.2 | 75.6 | 73.9 |
| S043667CFB | 36.3 | 39.4 | 38.1 | 53.1 | 23.4 | 49.9 | 40.0 | 75.2 | 73.5 |
| S043961C | 33.8 | 47.8 | 60.0 | 32.2 | 19.4 | 39.3 | 38.7 | 72.8 | 71.2 |
| S044147FB | 33.5 | 42.3 | 26.8 | 45.8 | 18.9 | 40.0 | 34.5 | 64.9 | 63.4 |
| Check Mean | 49.0 | 67.7 | 57.3 | 53.9 | 33.3 | 65.3 | 54.4 | 0.0 | 0.0 |
| CV | 12.6 | 16.6 | 15.4 | 17.6 | 13.0 | 9.9 | 18.6 | 0.0 | 0.0 |
| Grand Mean | 46.4 | 59.2 | 58.5 | 55.0 | 36.5 | 63.6 | 53.2 | 0.0 | 0.0 |
| Heritability | 0.5 | 0.4 | 0.5 | 0.4 | 0.9 | 0.6 | 0.5 | 0.0 | 0.0 |
| LSD | 9.9 | 16.5 | 15.1 | 16.3 | 8.0 | 10.6 | 6.6 | 0.0 | 0.0 |
| R-Square | 0.8 | 0.7 | 0.7 | 0.7 | 0.9 | 0.8 | 0.6 | 0.0 | 0.0 |
| Residual | 34.3 | 96.3 | 80.8 | 93.5 | 22.4 | 39.7 | 97.5 | 0.0 | 0.0 |
| SED | 5.9 | 9.8 | 9.0 | 9.7 | 4.7 | 6.3 | 9.9 | 0.0 | 0.0 |

Table 11 shows the results obtained from a trial conducted over six locations (Cleveland, Miss.; Clarksdale, Miss.; DeWitt, Ark.; Keiser, Ark.; Morganza, La.; and Weiner, Ark.) in 2008 for various agronomic characteristics. Column 1 shows the variety name, column 2 shows the plant habit from DeWitt, column 3 shows the pubescence/pod color from DeWitt (where pubescence is characterized as G=Gray, T=Tawny (Brown), or LT=Light Tawny, and where pod color is characterized as T=Tan or B=Brown), column 4 shows the maturity date from DeWitt, column 5 shows the average plant height in inches from all six locations, and column 6 shows the average lodging score from all six locations.

TABLE 11

| VARIETY | DW H | DW PUB/POD | DW MD | AVG PH | AVG LDG |
|---|---|---|---|---|---|
| 3317361 | DET | T/T | 10/1 | 34 | 1.9 |
| S044076C | DET | T/T | 10/1 | 29 | 1.2 |
| S000875 | DET | G/T | 10/2 | 29 | 2.3 |
| S043702C | DET | T/T | 10/1 | 31 | 1.7 |
| S022010 | DET | T/T | 9/30 | 34 | 1.4 |
| R01-3474F | DET | G/T | 10/1 | 31 | 1.7 |
| S001185 | DET | T/T | 10/1 | 34 | 1.5 |
| S043791C | DET | T/T | 10/1 | 41 | 2.3 |
| S011241 | IND | G/T | 9/29 | 50 | 2.2 |
| S043785C | DET | T/T | 10/15 | 36 | 1.5 |
| S001177 | DET | T/T | 10/1 | 33 | 1.5 |
| NC ROY | DET | LT/B | 10/1 | 34 | 2.5 |
| S001189 | DET | G/T | 9/30 | 31 | 2.0 |
| TN 5601T | DET | G/T | 10/1 | 30 | 1.4 |
| S044063C | IND | LT/T | 10/1 | 44 | 2.0 |
| S022395 | DET | T/T | 10/12 | 31 | 1.7 |
| S022460 | DET | T/T | 10/1 | 36 | 1.4 |
| HBK 5991 | DET | T/T | 10/1 | 30 | 1.4 |
| S022279 | DET | G/T | 10/1 | 32 | 1.7 |
| S032596 | DET | G/T | 10/2 | 36 | 1.6 |
| OZARK | DET | G/T | 10/1 | 27 | 1.7 |
| S043783C | DET | G/T | 10/1 | 30 | 1.3 |
| S022012 | DET | T/T | 10/1 | 32 | 1.5 |
| S043756C | DET | T/T | 10/1 | 26 | 1.3 |
| S044043C | DET | T/T | 10/1 | 35 | 2.3 |
| S044064C | IND | T/T | 10/1 | 44 | 2.2 |
| S022009 | DET | G/T | 9/29 | 32 | 2.4 |
| S043792C | DET | T/T | 10/1 | 31 | 1.4 |
| S043496C | DET | T/T | 9/28 | 28 | 2.0 |

TABLE 11-continued

| VARIETY | DW H | DW PUB/POD | DW MD | AVG PH | AVG LDG |
|---|---|---|---|---|---|
| S043629CFB | DET | G/T | 10/2 | 33 | 2.1 |
| S043627CFB | DET | G/T | 10/1 | 34 | 2.2 |
| S044122FB | DET | G/T | 10/1 | 34 | 1.7 |
| S043494C | DET | T/T | 9/29 | 27 | 1.7 |
| S043943C | IND | G/T | 9/27 | 48 | 2.6 |
| S044077C | DET | T/T | 10/1 | 23 | 1.0 |
| S04-9344 | DET | G/T | 10/1 | 21 | 1.3 |
| S043670CFB | DET | G/T | 10/2 | 33 | 2.4 |
| S043667CFB | DET | G/T | 10/1 | 33 | 2.0 |
| S043961C | IND | T/T | 9/30 | 41 | 1.8 |
| S044147FB | DET | LT/ | 9/25 | 30 | 1.5 |

Table 12 shows the results obtained from a trial conducted over four locations (DeWitt, Ark.; Eudora, Ark.; Holandale, Miss.; and Waldenburg, Ark.) in 2004. The planting dates were May 16, May 21, May 5, and June 4, respectively. The harvest dates were October 29, November 12, September 28, and November 7, respectively. All yield was calculated as bushels per acre. Column 1 shows the variety name, column 2 shows the mean yield from DeWitt (which is a light soil location), column 3 shows the mean yield from Eudora (which is a heavy clay soil location), column 4 shows the shows the mean yield from Holandale (which is a heavy clay soil location), column 5 shows the shows the mean yield from Waldenburg (which is a light soil location), column 6 shows the mean yield of all four locations (columns 2-5), column 7 shows the mean yield from heavy clay soil locations (Eudora and Holandale), column 8 shows the mean yield from light soil locations (DeWitt and Waldenburg), column 9 shows the mean yield of the variety as a percentage of the grand mean yield, and column 10 shows the mean yield as a percentage of the check mean yield.

TABLE 12

| VARIETY | DW LT | EA HV | HE HV | WG LT | MEAN OF 4 LOC | AVG ON HEAVY SOILS | AVG ON LIGHT SOILS | % OF GRAND MEAN | % OF CHECK MEAN |
|---|---|---|---|---|---|---|---|---|---|
| 3317361 | 75.4 | 49.9 | 70.8 | 52.2 | 62.1 | 60.4 | 63.8 | 121.6 | 110.7 |
| CS R5952N | 80.8 | 42.7 | 66.0 | 62.0 | 62.9 | 54.4 | 71.4 | 123.2 | 112.1 |
| S032484 | 67.4 | 45.5 | 70.7 | 57.4 | 60.3 | 58.1 | 62.4 | 118.1 | 107.4 |
| S032483 | 75.1 | 53.9 | 59.2 | 52.2 | 60.1 | 56.6 | 63.7 | 117.8 | 107.1 |
| A 5427 | 67.4 | 45.1 | 58.4 | 65.6 | 59.1 | 51.8 | 66.5 | 115.9 | 105.4 |
| CS R5722N | 76.9 | 42.6 | 58.8 | 58.0 | 59.1 | 50.7 | 67.5 | 115.8 | 105.3 |
| S032449 | 66.6 | 51.6 | 62.7 | 55.1 | 59.0 | 57.2 | 60.9 | 115.6 | 105.2 |
| S032486 | 75.4 | 45.4 | 65.3 | 47.6 | 58.4 | 55.4 | 61.5 | 114.5 | 104.2 |
| S032468 | 73.5 | 41.7 | 62.2 | 55.8 | 58.3 | 52.0 | 64.7 | 114.3 | 103.9 |
| A 5959 | 63.5 | 46.6 | 59.2 | 56.6 | 56.5 | 52.9 | 60.1 | 110.7 | 100.7 |
| S032466 | 77.7 | 39.6 | 57.7 | 50.2 | 56.3 | 48.7 | 64.0 | 110.3 | 100.4 |
| S032469 | 64.7 | 52.8 | 52.5 | 53.0 | 55.8 | 52.7 | 58.9 | 109.3 | 99.4 |
| S032464 | 70.1 | 32.4 | 64.0 | 56.2 | 55.7 | 48.2 | 63.2 | 109.1 | 99.3 |
| S032440 | 59.8 | 24.9 | 65.3 | 69.5 | 54.9 | 45.1 | 64.7 | 107.5 | 97.8 |
| ANAND | 72.9 | 40.2 | 47.5 | 56.8 | 54.4 | 43.9 | 64.9 | 106.5 | 96.9 |
| HBK 5991 | 64.1 | 30.6 | 66.9 | 53.1 | 53.7 | 48.8 | 58.6 | 105.2 | 95.7 |
| S032480 | 60.7 | 32.1 | 69.3 | 52.2 | 53.6 | 50.7 | 56.5 | 105.0 | 95.5 |
| S032439 | 60.1 | 43.7 | 46.2 | 57.2 | 51.8 | 45.0 | 58.7 | 101.5 | 92.4 |
| P 95B97 | 61.5 | 37.5 | 51.1 | 56.6 | 51.7 | 44.3 | 59.1 | 101.3 | 92.1 |
| S032458 | 54.2 | 37.3 | 62.5 | 51.9 | 51.5 | 49.9 | 53.1 | 100.9 | 91.8 |
| P 9594 | 57.3 | 19.6 | 78.6 | 50.5 | 51.5 | 49.1 | 53.9 | 100.9 | 91.8 |
| S032462 | 50.7 | 46.4 | 56.7 | 48.3 | 50.5 | 51.6 | 49.5 | 99.0 | 90.1 |
| S032475 | 57.6 | 42.3 | 52.1 | 44.1 | 49.0 | 47.2 | 50.9 | 96.1 | 87.4 |
| S032457 | 58.2 | 35.1 | 46.7 | 55.6 | 48.9 | 40.9 | 56.9 | 95.8 | 87.2 |
| S032472 | 60.7 | 45.7 | 42.8 | 44.2 | 48.4 | 44.3 | 52.5 | 94.8 | 86.2 |
| S032459 | 54.4 | 40.4 | 54.7 | 42.3 | 48.0 | 47.6 | 48.4 | 94.0 | 85.5 |
| S032456 | 60.0 | 35.2 | 50.8 | 45.0 | 47.8 | 43.0 | 52.5 | 93.6 | 85.1 |
| S032451 | 64.4 | 25.7 | 47.9 | 51.4 | 47.4 | 36.8 | 57.9 | 92.8 | 84.4 |
| S032454 | 60.4 | 24.9 | 55.6 | 45.2 | 46.5 | 40.3 | 52.8 | 91.2 | 82.9 |
| S032444 | 69.6 | 37.2 | 29.0 | 49.7 | 46.4 | 33.1 | 59.7 | 90.9 | 82.7 |
| S032443 | 54.5 | 35.0 | 46.1 | 47.9 | 45.9 | 40.6 | 51.2 | 89.9 | 81.8 |
| S032447 | 56.6 | 35.0 | 43.0 | 46.3 | 45.2 | 39.0 | 51.5 | 88.6 | 80.6 |
| S032453 | 54.5 | 17.8 | 57.5 | 49.5 | 44.8 | 37.7 | 52.0 | 87.8 | 79.9 |
| S032445 | 50.1 | 29.1 | 51.4 | 48.1 | 44.7 | 40.3 | 49.1 | 87.6 | 79.6 |
| S032452 | 56.6 | 22.3 | 48.3 | 51.3 | 44.6 | 35.3 | 54.0 | 87.5 | 79.6 |
| S032446 | 58.0 | 23.9 | 39.5 | 47.1 | 42.1 | 31.7 | 52.6 | 82.6 | 75.1 |
| S032481 | 56.3 | 27.4 | 33.5 | 47.0 | 41.1 | 30.5 | 51.7 | 80.4 | 73.2 |
| S032448 | 46.9 | 28.3 | 39.7 | 48.8 | 40.9 | 34.0 | 47.9 | 80.2 | 73.0 |
| S032441 | 38.6 | 31.8 | 41.9 | 42.4 | 38.7 | 36.9 | 40.5 | 75.8 | 69.0 |
| S032477 | 36.8 | 33.6 | 25.4 | 40.6 | 34.1 | 29.5 | 38.7 | 66.8 | 60.8 |
| Grand Mean | 61.8 | 36.8 | 53.9 | 51.6 | 51.0 | 45.4 | 56.7 | | |
| Check Mean | 68.1 | 38.1 | 60.8 | 57.4 | 56.1 | | | | |
| % CV | 16 | 25.1 | 21.6 | 11.9 | 14.9 | | | | |
| Heritability | 0 | 0 | 0 | 0 | 0.4 | | | | |
| LSD | 0 | 0 | 0 | 0 | 8.9 | | | | |
| R-Square | 0 | 0 | 0 | 0 | 0.8 | | | | |
| Residual | 97.9 | 85.4 | 135.1 | 37.7 | 58 | | | | |
| SED | 14 | 13.1 | 16.4 | 8.7 | 5.4 | | | | |

Table 13 shows the results obtained from a trial conducted over four locations (DeWitt, Ark.; Eudora, Ark.; Holandale, Miss.; and Waldenburg, Ark.) in 2004 for various agronomic characteristics. Column 1 shows the variety name, column 2 shows the plant habit from DeWitt, column 3 shows the pubescence/pod color from DeWitt (where pubescence is characterized as G=Gray, T=Tawny (Brown), or LT=Light Tawny, and where pod color is characterized as T=Tan or B=Brown), column 4 shows the maturity date from DeWitt, column 5 shows the average plant height in inches from all four locations, and column 6 shows the average lodging score from all four locations.

TABLE 13

| VARIETY | DW H | DW PUB/POD | DW MD | AVG PH | AVG LDG |
|---|---|---|---|---|---|
| 3317361 | DET | T/T | 9/27 | 33 | 1.0 |
| CS R5952N | DET | G/T | 9/30 | 35 | 1.1 |
| S032484 | DET | T/T | 9/28 | 29 | 1.4 |
| S032483 | DET | T/T | 9/30 | 30 | 1.4 |
| A 5427 | DET | G/T | 9/24 | 27 | 1.0 |
| CS R5722N | DET | G/T | 9/27 | 32 | 1.4 |
| S032449 | DET | T/T | 9/27 | 33 | 1.5 |
| S032486 | DET | T/T | 9/29 | 32 | 1.4 |
| S032468 | DET | G/T | 9/28 | 27 | 1.0 |
| A 5959 | DET | G/T | 9/28 | 30 | 1.8 |
| S032466 | DET | LT/T | 9/30 | 28 | 1.1 |
| S032469 | DET | T/T | 9/27 | 29 | 1.3 |
| S032464 | DET | G/T | 10/1 | 31 | 1.5 |
| S032440 | DET | G/T | 9/27 | 32 | 1.8 |
| ANAND | DET | T/T | 9/25 | 27 | 1.0 |
| HBK 5991 | DET | T/T | 9/27 | 31 | 1.6 |
| S032480 | DET | T/T | 9/26 | 28 | 1.9 |
| S032439 | DET | G/T | 9/27 | 26 | 1.3 |
| P 95B97 | DET | G/T | 9/27 | 30 | 2.3 |
| S032458 | DET | G/T | 10/5 | 32 | 1.3 |

TABLE 13-continued

| VARIETY | DW H | DW PUB/POD | DW MD | AVG PH | AVG LDG |
|---|---|---|---|---|---|
| P 9594 | DET | G/T | 9/28 | 32 | 1.9 |
| S032462 | DET | G/T | 10/3 | 38 | 1.7 |
| S032475 | DET | G/T | 9/30 | 33 | 1.0 |
| S032457 | DET | G/T | 9/28 | 28 | 1.4 |
| S032472 | DET | T/T | 10/5 | 33 | 1.4 |
| S032459 | DET | G/T | 10/6 | 36 | 1.4 |
| S032456 | IND | LT/B | 9/30 | 51 | 2.3 |
| S032451 | DET | T/T | 9/28 | 31 | 2.5 |
| S032454 | DET | T/T | 9/25 | 31 | 2.6 |
| S032444 | DET | T/T | 10/2 | 32 | 1.6 |
| S032443 | DET | T/T | 9/28 | 31 | 1.9 |
| S032447 | DET | T/T | 9/26 | 30 | 1.1 |
| S032453 | DET | T/T | 9/29 | 36 | 1.9 |
| S032445 | DET | T/T | 9/30 | 32 | 1.8 |
| S032452 | DET | T/T | 9/28 | 32 | 2.8 |
| S032446 | DET | T/T | 9/27 | 34 | 2.0 |
| S032481 | DET | T/T | 9/26 | 26 | 1.4 |
| S032448 | DET | T/T | 9/27 | 34 | 1.5 |
| S032441 | IND | G/T | 9/27 | 38 | 2.5 |
| S032477 | DET | G/T | 10/5 | 37 | 2.0 |

Deposit Information

A deposit of the soybean seed of this invention is maintained by Hornbeck Seed Co., Inc., P.O. Box 472, 210 Drier Road, DeWitt, Ark. 72042. Access to this deposit will be available during the pendency of this application to persons determined by the Commissioner of Patents and Trademarks to be entitled thereto under 37 C.F.R. §1.14 and 35 U.S.C. §122. Representative seeds of Soybean Cultivar 3317361 were deposited on Aug. 8, 2012 with the American Type Culture Collection, 10801 University Blvd, Manassas, Va. 20110 under ATCC Accession No. PTA-13124. Upon allowance of any claims in this application, all restrictions on the availability to the public of the variety will be irrevocably removed by affording access to this deposit with the American Type Culture Collection, Manassas, Va.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

What is claimed is:

1. A seed of soybean cultivar 3317361, representative sample seed of said cultivar is deposited under ATCC Accession No. PTA-13124.

2. A soybean plant, or a part thereof, produced by growing the seed of claim 1.

3. A tissue culture produced from protoplasts or cells from the plant of claim 2, wherein said cells or protoplasts are produced from a plant part selected from the group consisting of leaf, pollen, ovule, embryo, cotyledon, hypocotyl, meristematic cell, root, root tip, pistil, anther, flower, seed, shoot, stem, pod and petiole.

4. A soybean plant regenerated from the tissue culture of claim 3, wherein said soybean plant has all of the physiological and morphological characteristics of the plant of claim 2.

5. A method for producing a soybean seed, comprising crossing two soybean plants and harvesting the resultant soybean seed, wherein at least one soybean plant is the soybean plant of claim 2.

6. A soybean seed produced by the method of claim 5.

7. A soybean plant, or a part thereof, produced by growing said seed of claim 6.

8. The method of claim 5, wherein at least one of said soybean plants further comprises at least one transgene.

9. A method of producing an herbicide resistant soybean plant, wherein said method comprises introducing a gene conferring herbicide resistance into the plant of claim 2.

10. A herbicide resistant soybean plant produced by the method of claim 9, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, and benzonitrile.

11. A method of producing a pest or insect resistant soybean plant, wherein said method comprises introducing a gene conferring pest or insect resistance into the soybean plant of claim 2.

12. A pest or insect resistant soybean plant produced by the method of claim 11.

13. The soybean plant of claim 12, wherein the gene encodes a *Bacillus thuringiensis* (Bt) endotoxin.

14. A method of producing a disease resistant soybean plant, wherein said method comprises introducing a gene which confers disease resistance into the soybean plant of claim 2.

15. A disease resistant soybean plant produced by the method of claim 14.

16. A method of producing a soybean plant with modified fatty acid metabolism or modified carbohydrate metabolism, wherein the method comprises introducing a gene encoding a protein selected from the group consisting of phytase, fructosyltransferase, levansucrase, .alpha.-amylase, invertase and starch branching enzyme or encoding an antisense of stearyl-ACP desaturase into the soybean plant of claim 2.

17. A soybean plant having modified fatty acid metabolism or modified carbohydrate metabolism produced by the method of claim 16.

18. A method of introducing a desired trait into soybean cultivar 3317361, wherein the method comprises:
(a) crossing a 3317361 plant, wherein a representative sample of seed is deposited under ATCC Accession No. PTA-13124, with a plant of another soybean cultivar that comprises a desired trait to produce progeny plants wherein the desired trait is selected from the group consisting of male sterility, herbicide resistance, insect resistance, modified fatty acid metabolism, modified carbohydrate metabolism, modified seed yield, modified oil percent, modified protein percent, modified lodging resistance, modified shattering, modified iron-deficiency chlorosis and resistance to bacterial disease, fungal disease or viral disease;
(b) selecting one or more progeny plants that have the desired trait to produce selected progeny plants;
(c) crossing the selected progeny plants with the 3317361 plant to produce backcross progeny plants;
(d) selecting for backcross progeny plants that have the desired trait and all of the physiological and morphological characteristics of soybean cultivar 3317361 listed in Table 1; and
(e) repeating steps (c) and (d) two or more times in succession to produce selected third or higher backcross progeny plants that comprise the desired trait and all of the physiological and morphological characteristics of soybean cultivar 3317361 listed in Table 1.

19. A soybean plant produced by the method of claim 18, wherein the plant has the desired trait.

20. The soybean plant of claim 19, wherein the desired trait is herbicide resistance and the resistance is conferred to an herbicide selected from the group consisting of imidazolinone, dicamba, cyclohexanedione, sulfonylurea, glyphosate, glufosinate, phenoxy proprionic acid, L-phosphinothricin, triazine and benzonitrile.

21. The soybean plant of claim 19, wherein the desired trait is insect resistance and the insect resistance is conferred by a gene encoding a *Bacillus thuringiensis* endotoxin.

22. The soybean plant of claim 19, wherein the desired trait is modified fatty acid metabolism or modified carbohydrate metabolism and said desired trait is conferred by a nucleic acid encoding a protein selected from the group consisting of phytase, fructosyltransferase, levansucrase, .alpha.-amylase, invertase and starch branching enzyme or encoding an antisense of stearyl-ACP desaturase.

23. A method of producing a commodity plant product, comprising obtaining the plant of claim 2, or a part thereof, wherein the commodity plant product is protein concentrate, protein isolate, soybean hulls, meal, flour, or oil and producing said commodity plant product therefrom.

* * * * *